United States Patent
Murray et al.

(10) Patent No.: US 6,365,347 B1
(45) Date of Patent: *Apr. 2, 2002

(54) METHOD FOR IDENTIFYING DISRUPTORS OF BIOLOGICAL PATHWAYS USING GENETIC SELECTION

(75) Inventors: Andrew W. Murray; Dana L. Smith, both of San Francisco, CA (US); Peter K. Sorger, Cambridge, MA (US); Thea C. Norman, San Francisco, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/058,483

(22) Filed: Apr. 10, 1998

Related U.S. Application Data

(63) Continuation-in-part of application No. 08/835,727, filed on Apr. 11, 1997, now abandoned.

(51) Int. Cl.$^7$ .......................... C12Q 1/68; C12N 15/11; C12N 15/63
(52) U.S. Cl. ...................... 435/6; 435/69.1; 435/320.1; 536/23.4; 536/24.1
(58) Field of Search .......................... 435/6, 69.2, 69.7, 435/91.41, 455, 468, 252.3, 254.11, 320.1, 235.1, 69.1; 530/350; 536/23.4, 24.1

(56) References Cited

U.S. PATENT DOCUMENTS

| | | | |
|---|---|---|---|
| 5,427,908 A | | 6/1995 | Dower et al. |
| 5,525,490 A | * | 6/1996 | Erickson et al. ............... 435/29 |
| 5,585,087 A | | 12/1996 | Lustig et al. |
| 5,639,858 A | | 6/1997 | Hoey et al. |
| 5,648,245 A | | 7/1997 | Fire et al. |
| 6,004,746 A | * | 12/1999 | Brent et al. ..................... 435/6 |
| 6,083,746 A | * | 7/2000 | Gudkov et al. ............. 435/325 |

FOREIGN PATENT DOCUMENTS

| | | |
|---|---|---|
| WO | WO 9603501 A1 * | 2/1996 |

OTHER PUBLICATIONS

LaVille et al. A Thioredoxin gen fusion expression system that circumvents inclusion body formation in the *E. coli* cytoplasm. Biothechnology vol. 11 pp. 187–193, 1993.*

Wotton et al. Miltimerization of Hsp42p, a novel heat shock protein of *Saccharomyces serevisiae*, is dependent on a conserved carboxyl–terminal sequence. J. Biol. Chem. vol. 271 pp. 2717–2723, 1996.*

Hardwick et al. Activation of the budding yeast spindly assembly checkpoint without mitotic spindle disruption. Science vol. 273 pp. 953–956, 1996.*

Huang et al. Identification of a novel protein kinase A anchoring protein that binds both thpe I and type II regulatory subunits. J. Biol. Chem. vol. 272 pp. 8057–8064, 1997.*

Weinert et al. Mitotic checkpoint genes in budding yeast and the dependence of mitosis on DNA replication and repair. Genes and Development vol. 8 pp. 652–665, 1994.*

Manfredi et al. Yeast alpha mating factor structure–activity relationship derived from genetically selected peptide agonists and antagonists of ste2p. Molec. Cell. Biol. vol. 16 pp. 4700–4709, 1996.*

Yavuzer et al. pWITCH: a versatile two–hybrid assay vector for the production of epitope/activation domain–tagged proteins both in vitro and in yeast. Gene vol. 165 pp. 93–96, 1995.*

Benediktsson et al. Studies of the mechanism of transgene integration into plant protoplasts: improvement of the transformation rate. Euphytica vol. 85 pp. 53–61, 1995.*

Fearon et al. Karyoplasmic interaction selection strategy: A general strategy to detect protein–protein interactions in mammalian cells. Proc. Natl. Acad. Sci. USA vol. 89 pp. 7958–7962, 1992.*

Chakraborty et al. Analysos of the oligomerization of myogenin and E2A products in vivo using a two–hybrid assay systems. J. Biol Chem. vol. 267 pp. 17498–17501, 1992.*

Yang et al. Protein–peptide interactions analyzed with the yeast two–hybrid system. Nucleic Acids Research vol. 23 pp. 1152–1156, 1995.*

Colas et al. Genetic selection of peptide aptamers that recognize and inhibit cyclin–dependent kinase 2. Nature vol. 380 pp. 548–550, 1996.*

Hannon et al. Isolation of the Rb–related p130 through its interaction with CDK2 and cyclins. Genes and Development vol. 7 pp. 2378–2391, 1993.*

Orkin et al. report and recommendations of the panel assess the NIH investment in research on gene therapy. pp. 1–41, 1995.*

* cited by examiner

Primary Examiner—John S. Brusca
(74) Attorney, Agent, or Firm—Mandel & Adriano

(57) ABSTRACT

Macromolecule libraries constructed by transforming host cells with a collection of recombinant vectors that encode chimeras comprised of a carrier protein and a random peptide sequence are generated. The chimera is expressed intracellularly so that peptide inhibitors of biological pathways are identified through genetic selection. Peptides having a wide variety of uses such as therapeutic of diagnostic reagents, may thus be identified without any prior information on the structure of the desired target for the chimera.

16 Claims, 14 Drawing Sheets

FIG. 1A

MLVMTEYLLSAGICMAIVSILLIGMAISNVSKGQYAKRFFFFATSCLVLTLVVVSSLSSSANASQ
TDNGVNRSGSEDPTVYSATSTKKLHKEPATLIKAIDGDTVKLMYKGQPMTFRLLLVDTPETKHPK
KGVEKYGPEASAFTKKMVENAKKIEVEFDKGQRTDKYGRGLAYIYADGKMVNEALVRQGLAKVAY
VYKPNNTHEQHLRKSEAQAKKEKLNIWSEDNADSGQ

FIG. 1B

SATSTKKLHKEPATLIKAIDGDTVKLMYKGQPMTFRLLLVDTPETKHPKKGVEKYGPEASAFTKK
MVENAKKIEVEFDKGQRTDKYGRGLAYIYADGKMVNEALVRQGLAKVAYVYKPNNTHEQHLRKSE
AQAKKEKLNIWSEDNADSGQ

FIG. 2A

MYPYDVPDYASLPGIQPATSTKKLHKEPATLIKAIDGTTVKLMYKGQPMTFRLLLVDTPEFKAKS
PKKALEKYGPEASAFTKKMVENAKKIEVEFDKGQRTDKYGRGLAYIYADGKMVNEALVRQGLAKV
AYVYKPNNTHEQHLRKSEAQAKKEKLNIWSEDNADSGQVDVHHHHHH

FIG. 2B

YPYDVPDYASLP

FIG. 2C

TPEFKAKSPKKA

FIG. 2D

HHHHHH

FIG. 3A-1

```
GAATTAATTCCACCGCGGTGGCGGCCAATTCTCATGTTTGACAGCTTATCATCGATGGATAAGCA
TGAATATCGGCTTCGCGGTCACAGCACGCATCACGTTGCTCATCATGCTGCCCATGCGTAACCGG
CTAGTTGCGGCCGCTGCCAGCCATTTGCCACTCTCCTTTTCATCCGCATCGGCAGGGTCATCCGG
GCGCATCCACCACTCCTGATGCAGTAATCCTACGGTGCGGAATGTGGTGGCCTCGAAATTCTGTC
ATAAAGTTGTCACGGCCGAGACTTATAGTCGCTTTGTTTTTATTTTTTAATGTATTTGTACATGG
AGAAAATAAAGTGAAACAAACGACTATTGCACTGGCACTCTTACCGTTACTGTTTACCCCTGTGA
CAAAAGCCCGGATCCCCAATTCACTGGCCGTCGTTTTACAACGTCGTGACTGGGAAAACCCTGGC
GTTACCCAACTTAATCGCCTTGCAGCACATCCCCCTTTCGCCAGCTGGCGTAATAGCGAAGAGGC
CCGCACCGATCGCCCTTCCCAACAGTTGCGCAGCCTGAATGGCGAATGGCGCCTGATGCGGTATT
TTCTCCTTACGCATCTGTGCGGTATTTCACACCGCATATATCGCTGGGCCATTCTCATGAAGAAT
ATCTTGAATTTATTGTCATATTACTAGTTGGTGTGGAAGTCCATATATCGGTGATCAATATAGTG
GTTGACATGCTGGCTAGTCAACATTGAGCCTTTTGATCATGCAAATATATTACGGTATTTTACAA
TCAAATATCAAACTTAACTATTGACTTTATAACTTATTTAGGTGGTAACATTCTTATAAAAAAGA
AAAAAATTACTGCAAAACAGTACTAGCTTTTAACTTGTATCCTAGGTTATCTATGCTGTCTCACC
ATAGAGAATATTACCTATTTCAGAATGTATGTCCATGATTCGCCGGGTAAATACATATAATACAC
AAATCTGGCTTAATAAAGTCTATAATATATCTCATAAAGAAGTGCTAAATTGGCTAGTGCTATAT
ATTTTTAAGAAAATTTCTTTTGACTAAGTCCATATCGACTTTGTAAAAGTTCACTTTAGCATACA
TATATTACACGAGCCAGAAATTGTAACTTTTGCCTAAAATCACAAATTGCAAAATTTAATTGCTT
GCAAAAGGTCACATGCTTATAATCAACTTTTTTAAAAATTTAAAATACTTTTTATTTTTTATTT
TTAAACATAAATGAAATAATTTATTTATTGTTTATGATTACCGAAACATAAAACCTGCTCAAGAA
AAAGAAACTGTTTTGTCCTTGGAAAAAAAGCACTACCTAGGAGCGGCCAAAATGCCGAGGCTTTC
ATAGCTTAAACTCTTTACAGAAAATAGGCATTATAGATCAGTTCGAGTTTTCTTATTCTTCCTTC
CGGTTTTATCGTCACAGTTTTACAGTAAATAAGTATCACCTCTTAGAGTTCGATGATAAGCTGTC
AAACATGAGAATTAATTCCACATGTTAAAATAGTGAAGGAGCATGTTCGGCACACAGTGGACCGA
ACGTGGGGTAAGTGCACTAGGGTCCGGTTAAACGGATCTCGCATTGATGAGGCAACGCTAATTAT
CAACATATAGATTGTTATCTATCTGCATGAACACGAAATCTTTACTTGACGACTTGAGGCTGATG
GTGTTTATGCAAAGAAACCACTGTGTTTAATATGTGTCACTGTTTGATATTACTGTCAGCGTAGA
AGATAATAGTAAAAGCGGTTAATAAGTGTATTTGAGATAAGTGTGATAAAGTTTTTACAGCGAAA
AGACGATAAATACAAGAAAATGATTACGAGGATACGGAGAGAGGTATGTACATGTGTATTTATAT
ACTAAGCTGCCGGCGGTTGTTTGCAAGACCGAGAAAAGGCTAGCAAGAATCGGGTCATTGTAGCG
TATGCGCCTGTGAACATTCTCTTCAACAAGTTTGATTCCATTGCGGTGAAATGGTAAAAGTCAAC
CCCCTGCGATGTATATTTTCCTGTACAATCAATCAAAAAGCCAAATGATTTAGCATTATCTTTAC
ATCTTGTTATTTTACAGATTTTATGTTTAGATCTTTTATGCTTGCTTTTCAAAAGGCTTGCAGGC
AAGTGCACAAACAATACTTAAATAAATACTACTCAGTAATAACCTATTTCTTAGCATTTTTGACG
AAATTTGCTATTTTGTTAGAGTCTTTTACACCATTTGTCTCCACACCTCCGCTTACATCAACACC
AATAACGCCATTTAATCTAAGCGCATCACCAACATTTTCTGGCGTCAGTCCACCAGCTAACATAA
AATGTAAGCTCTCGGGGCTCTCTTGCCTTCCAACCCAGTCAGAAATCGAGTTCCAATCCAAAAGT
TCACCTGTCCCACCTGCTTCTGAATCAAACAAGGGAATAAACGAATGAGGTTTCTGTGAAGCTGC
ACTGAGTAGTATGTTGCAGTCTTTTGGAAATACGAGTCTTTTAATAACTGGCAAACCGAGGAACT
CTTGGTATTCTTGCCACGACTCATCTCCATGCAGTTGGACGATCGATGATAAGCTGTCAAACATG
```

FIG. 3A-2

```
AGAATTGGGTAATAACTGATATAATTAAATTGAAGCTCTAATTTGTGAGTTTAGTATACATGCAT
TTACTTATAATACAGTTTTTTAGTTTTGCTGGCCGCATCTTCTCAAATATGCTTCCCAGCCTGCT
TTTCTGTAACGTTCACCCTCTACCTTAGCATCCCTTCCCTTTGCAAATAGTCCTCTTCCAACAAT
AATAATGTCAGATCCTGTAGAGACCACATCATCCACGGTTCTATACTGTTGACCCAATGCGTCTC
CCTTGTCATCTAAACCCACACCGGGTGTCATAATCAACCAATCGTAACCTTCATCTCTTCCACCC
ATGTCTCTTTGAGCAATAAAGCCGATAACAAAATCTTTGTCGCTCTTCGCAATGTCAACAGTACC
CTTAGTATATTCTCCAGTAGATAGGGAGCCCTTGCATGACAATTCTGCTAACATCAAAAGGCCTC
TAGGTTCCTTTGTTACTTCTTCTGCCGCCTGCTTCAAACCGCTAACAATACCTGGGCCCACCACA
CCGTGTGCATTCGTAATGTCTGCCCATTCTGCTATTCTGTATACACCCGCAGAGTACTGCAATTT
GACTGTATTACCAATGTCAGCAAATTTTCTGTCTTCGAAGAGTAAAAAATTGTACTTGGCGGATA
ATGCCTTTAGCGGCTTAACTGTGCCCTCCATGGAAAAATCAGTCAAGATATCCACATGTGTTTTT
AGTAAACAAATTTTGGGACCTAATGCTTCAACTAACTCCAGTAATTCCTTGGTGGTACGAACATC
CAATGAAGCACACAAGTTTGTTTGCTTTTCGTGCATGATATTAAATAGCTTGGCAGCAACAGGAC
TAGGATGAGTAGCAGCACGTTCCTTATATGTAGCTTTCGACATGATTTATCTTCGTTTCCTGCAG
GTTTTTGTTCTGTGCAGTTGGGTTAAGAATACTGGGCAATTTCATGTTTCTTCAACACCACATAT
GCGTATATATACCAATCTAAGTCTGTGCTCCTTCCTTCGTTCTTCCTTCTGCTCGGAGATTACCG
AATCAAAAAAATTTCAAAGAAACCGGAATCAAAAAAAAGAACAAAAAAAAAAAAAGATGAATTGAA
AAGCTTATCGATACCGTCGACTGCTCATTGCTATATTGAAGTACGGATTAGAAGCCGCCGAGCGG
GTGACAGCCCTCCGAAGGAAGACTCTCCTCCGTGCGTCCTCGTCTTCACCGGTCGCGTTCCTGAA
ACGCAGATGTGCCTCGCGCCGCACTGCTCCGAACAATAAAGATTCTACAATACTAGCTTTTATGG
TTATGAAGAGGAAAAATTGGCAGTAACCTGGCCCCACAAACCTTCAAATGAACGAATCAAATTAA
CAACCATAGGATGATAATGCGATTAGTTTTTTAGCCTTATTTCTGGGGTAATTAATCAGCGAAGC
GATGATTTTTGATCTATTAACAGATATATAAATGCAAAAACTGCATAACCACTTTAACTAATACT
TTCAACATTTTCGGTTTGTATTACTTCTTATTCAAATGTAATAAAAGTATCAACAAAAAATTGTT
AATATACCTCTATACTTTAACGTCAAGGAGAAAAAATATTAATGTACCCATATGATGTTCCAGAT
TACGCTTCTTTGCCCGGGATCCAGCCGGCAACTTCAACTAAAAAATTACATAAAGAACCTGCGAC
TTTAATTAAAGCGATTGATGGTACCACGGTTAAATTAATGTACAAAGGTCAACCAATGACATTCA
GACTATTATTGGTTGATACACCTGAATTCAAGGCTAAGTCTCCAAAGAAGGCTCTCGAGAAATAT
GGTCCTGAAGCAAGTGCATTTACGAAAAAAATGGTAGAAAATGCAAAGAAAATTGAAGTCGAGTT
TGACAAAGGTCAAAGAACTGATAAATATGGACGTGGCTTAGCGTATATTTATGCTGATGGAAAAA
TGGTAAACGAAGCTTTAGTTCGTCAAGGCTTGGCTAAAGTTGCTTATGTTTACAAACCTAACAAT
ACACATGAACAACATTTAAGAAAAAGTGAAGCACAAGCGAAAAAAGAGAAATTAAATATTTGGAG
CGAAGACAACGCTGATTCAGGTCAAGTCGACGTCCATCACCATCACCATCACTAATGCTCATTGT
AAAAGTGTCACTGCTGCTAGTGGCACTTTTATAATTTTTAGATCCTCTACGCCGGACGCATCGTG
GCCGGCATCACCGGCGCCACAGGTGCGGTTGCTGGCGCCTATATCGCCGACATCACCGATGGGGA
AGATCGGGCTCGCCACTTCGGGCTCATGAGCGCTTGTTTCGGCGTGGGTATGGTGGCAGGCCCCG
TGGCCGGGGGACTGTTGGGCGCCATCTCCTTGCATGCACCATTCCTTGCGGCGGCGGTGCTCAAC
GGCCTCAACCTACTACTGGGCTGCTTCCTAATGCAGGAGTCGCATAAGGGAGAGCGTCGACCTGC
CTCGCGCGTTTCGGTGATGACGGTGAAAACCTCTGACACATGCAGCTCCCGGAGACGGTCACAGC
TTGTCTGTAAGCGGATGCCGGGAGCAGACAAGCCCGTCAGGGCGCGTCAGCGGGTGTTGGCGGGT
```

FIG. 3A-3

```
GTCGGGGCGCAGCCATGACCCAGTCACGTAGCGATAGCGGAGTGTATACTGGCTTAACTATGCGG
CATCAGAGCAGATTGTACTGAGAGTGCACCATATGCGGTGTGAAATACCGCACAGATGCGTAAGG
AGAAAATACCGCATCAGGCGCTCTTCCGCTTCCTCGCTCACTGACTCGCTGCGCTCGGTCGTTCG
GCTGCGGCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCCGCGTTG
CTGGCGTTTTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTC
ACGTTAAGGGATTTTGGTCATGAGATTATCAAAAAGGATCTTCACCTAGATCCTTTTAAATTAAA
AATGAAGTTTTAAATCAATCTAAAGTATATATGAGTAAACTTGGTCTGACAGTTACCAATGCTTA
ATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAG
ACCCACGCTCACCGGCTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCGGGAAGCTAGAGTAAG
TAGTTCGCCAGTTAATAGTTTGCGCAACGTTGTTGCCATTGCTGCAGGCATCGTGGTGTCACGCT
CGTCGTTTGGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAGTTGGCCGC
AGTGTTATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGACCGAGT
TGCTCTTGCCCGGCGTCAACACGGGATAATACCGCGCCACATAGCAGAACTTTAAAAGTGCTCAT
CATTGGAAAACGTTCTTCGGGGCGAAAACTCTCAAGGATCTTACCGCTGTTGAGATCCAGTTCGA
TGTAACCCACTCGTGCACCCAACTGATCTTCAGCATCTTTTACTTTCACCAGCGTTTCTGGGTGA
GCAAAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGATACA
TATTTGAATGTATTTAGAAAAATAAACAAATAGGGGTTCCGCGCACATTTCCCCGAAAAGTGCCA
CCTGACGTCTAAGAAACCATTATTATCATGACATTAACCTATAAAAATAGGCGTATCACGAGGCC
CTTTCGTCTTCAA
```

FIG. 3B

| | |
|---:|:---|
| 1-400: | PhoA promoter for expression in Bacteria. |
| 400-2540 CEN4 ARS1: | Centromere and replication origin for replication and segregation in yeast. |
| 2540-3721 URA3: | (translated counterclockwise) Ura3 gene for selection in yeast. |
| 3721-4242 pGAL: | Galactose promoter for regulated expression in yeast plus hemagluttinin derived epitope tag. |
| 4243-4706: | Nuclease coding sequence plus H6 tag. |
| 5061-7358: | pBR322 sequences, bacterial replication origin and selectable marker. |

FIG. 4-1

```
GAATTAATTCCACCGCGGTGGCGGCCAATTCTCATGTTTGACAGCTTATCATCGATGGATAAGCA
TGAATATCGGCTTCGCGGTCACAGCACGCATCACGTTGCTCATCATGCTGCCCATGCGTAACCGG
CTAGTTGCGGCCGCTGCCAGCCATTTGCCACTCTCCTTTTCATCCGCATCGGCAGGGTCATCCGG
GCGCATCCACCACTCCTGATGCAGTAATCCTACGGTGCGGAATGTGGTGGCCTCGAAATTCTGTC
ATAAAGTTGTCACGGCCGAGACTTATAGTCGCTTTGTTTTTATTTTTTAATGTATTTGTACATGG
AGAAAATAAAGTGAAACAAACGACTATTGCACTGGCACTCTTACCGTTACTGTTTACCCCTGTGA
CAAAAGCCCGGATCCAGCCGGCAACTTCAACTAAAAAATTACATAAAGAACCTGCGACTTTAATT
AAAGCGATTGATGGTACCACGGTTAAATTAATGTACAAAGGTCAACCAATGACATTCAGACTATT
ATTGGTTGATACACCTGAATTCAAGGCTAAGTCTCCAAAGAAGGCTCTCGAGAAATATGGTCCTG
AAGCAAGTGCATTTACGAAAAAAATGGTAGAAAATGCAAAGAAAATTGAAGTCGAGTTTGACAAA
GGTCAAAGAACTGATAAATATGGACGTGGCTTAGCGTATATTTATGCTGATGGAAAAATGGTAAA
CGAAGCTTTAGTTCGTCAAGGCTTGGCTAAAGTTGCTTATGTTTACAAACCTAACAATACACATG
AACAACATTTAAGAAAAAGTGAAGCACAAGCGAAAAAAGAGAAATTAAATATTTGGAGCGAAGAC
AACGCTGATTCAGGTCAAGTCGACGTCCATCACCATCACCATCACTAATGCTCATTGTAAAAGTG
TCACTGCTGCTAGTGGCACTTTTATAATTTTTAGATCCTCTACGCCGGACGCATCGTGGCCGGCA
TCACCGGCGCCACAGGTGCGGTTGCTGGCGCCTATATCGCCGACATCACCGATGGGGAAGATCGG
GCTCGCCACTTCGGGCTCATGAGCGCTTGTTTCGGCGTGGGTATGGTGGCAGGCCCCGTGGCCGG
GGGACTGTTGGGCGCCATCTCCTTGCATGCACCATTCCTTGCGGCGGCGGTGCTCAACGGCCTCA
ACCTACTACTGGGCTGCTTCCTAATGCAGGAGTCGCATAAGGGAGAGCGTCGACCTGCCTCGCGC
GTTTCGGTGATGACGGTGAAAACCTCTGACACATGCAGCTCCCGGAGACGGTCACAGCTTGTCTG
TAAGCGGATGCCGGGAGCAGACAAGCCCGTCAGGGCGCGTCAGCGGGTGTTGGCGGGTGTCGGGG
CGCAGCCATGACCCAGTCACGTAGCGATAGCGGAGTGTATACTGGCTTAACTATGCGGCATCAGA
GCAGATTGTACTGAGAGTGCACCATATGCGGTGTGAAATACCGCACAGATGCGTAAGGAGAAAAT
ACCGCATCAGGCGCTCTTCCGCTTCCTCGCTCACTGACTCGCTGCGCTCGGTCGTTCGGCTGCGG
CGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGT
TTTTCCATAGGCTCCGCCCCCTGACGAGCATCACAAAAATCGACGCTCAAGTCAGAGGTGGCGA
AACCCGACAGGACTATAAAGATACCAGGCGTTTCCCCCTGGAAGCTCCCTCGTGCGCTCTCCTGT
TCCGACCCTGCCGCTTACCGGATACCTGTCCGCCTTTCTCCCTTCGGGAAGCGTGGCGCTTTCTC
ATAGCTCACGCTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGTCCAACCCGGT
AAGACACGACTTATCGCCACTGGCAGCAGCCACTGGTAACAGGATTAGCAGAGCGAGGTATGTAG
GCGGTGCTACAGAGTTCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTCTTGATCCGGCAAACA
AACCACCGCTGGTAGCGGTGGTTTTTTTGTTTGCAAGCAGCAGATTACGCGCAGAAAAAAAGGAT
CTCAAGAAGATCCTTTGATCTTTTCTACGGGGTCTGACGCTCAGTGGAACGAAAACTCACGTTAA
GGGATTTTGGTCATGAGATTATCAAAAAGGATCTTCACCTAGATCCTTTTAAATTAAAAATGAAG
TTTTAAATCAATCTAAAGTATATATGAGTAAACTTGGTCTGACAGTTACCAATGCTTAATCAGTG
AGGCACCTATCTCAGCGATCTGTCTATTTCGTTCATCCATAGTTGCCTGACTCCCCGTCGTGTAG
ATAACTACGATACGGGAGGGCTTACCATCTGGCCCCAGTGCTGCAATGATACCGCGAGACCCACG
```

FIG. 4-2

```
CTCACCGGCTCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTGCAGGCATCGTGGTGTCACGCTCGTCGTT
TGGTATGGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGCAGTGTTA
TCACTCATGGTTATGGCAGCACTGCATAATTCTCTTACTGTCATGCCATCCGTAAGATGCTTTTC
TGTGACTGGTGAGTACTCAACCAAGTCATTCTGAGAATAGTGTATGCGGCGACCGAGTTGCTCTT
GCCCGGCGTCAACACGGGATAATACCGCGCCACATAGCAGAACTTTAAAAGTGCTCATCATTGGA
AAACGTTCTTCGGGGCGAAAACTCTCAAGGATCTTACCGCTGTTGAGATCCAGTTCGATGTAACC
CACTCGTGCACCCAACTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATACATATTTGA
ATGTATTTAGAAAAATAAACAAATAGGGGTTCCGCGCACATTTCCCCGAAAAGTGCCACCTGACG
TCTAAGAAACCATTATTATCATGACATTAACCTATAAAAATAGGCGTATCACGAGGCCCTTTCGT
CTTCAA
```

FIG. 5A

VKQTTIALALLPLLFTPVTKARIQPATSTKKLHKEPATLIKAIDGTTVKLMYKGQPMTFRLLLVD
TPEFKAKSPKKALEKYGPEASAFTKKMVENAKKIEVEFDKGQRTDKYGRGLAYIYADGKMVNEAL
VRQGLAKVAYVYKPNNTHEQHLRKSEAQAKKEKLNIWSEDNADSGQVDVHHHHHH

FIG. 5B

VKQTTIALALLPLLFTPVTKAR

FIG. 6

Top Strand:
AA TTC GGT GGT ACT ACT TAC GCT GAT TTT ATT GCT TCT GGT
AGA ACT GGT AGA AGA AAT GCT ATT CAT GAT GGT GGT C Bottom Strand:
TC GAG ACC ACC ATC ATG AAT AGC ATT TCT TCT ACC AGT TCT
ACC AGA AGC AAT AAA ATC AGC GTA AGT AGT ACC ACC G

FIG. 7

Top Strand:
AA TTC GGT GGT ACT ACT TAC GCT GAT TTT ATT GCT TCT GGT
AGA ACT GGT GGT GGT AAT GCT ATT CAT GAT GGT GGT C Bottom Strand:
TC GAG ACC ACC ATC ATG AAT AGC ATT ACC ACC ACC AGT TC
T ACC AGA AGC AAT AAA ATC AGC GTA AGT AGT ACC ACC G

FIG. 8A

TTYADFIASGRTGRRNAIHD

FIG. 8B

TTYADFIASGRTGGGNAIHD

FIG. 9

EFGQRRTSVSGAL

METHOD FOR IDENTIFYING DISRUPTORS OF BIOLOGICAL PATHWAYS USING GENETIC SELECTION

This application is a continuation-in-part of U.S. Ser. No. 08/835,727, filed Apr. 11, 1997, now abandoned. The contents of this application is hereby incorporated by reference.

Throughout this application various publications are referenced. The disclosures of these publications in their entireties are hereby incorporated by reference into this application in order to more fully describe the state of the art to which this invention pertains.

FIELD OF THE INVENTION

The present invention relates generally to recombinant DNA technology and, particularly, to methods for generating combinatorial macromolecule libraries and screening these libraries for peptides of interest via genetic selection.

BACKGROUND OF THE INVENTION

The identification and isolation of proteins involved in cellular regulatory control is fundamental to the understanding of a wide variety of cellular mechanisms. As many pathologies, such as oncogenesis, involve a breakdown of these regulatory mechanisms, the isolation of these proteins is a significant step in the process of discovering new therapeutics. One means of identifying these proteins involves the generation of peptides which inhibit regulatory mechanisms by acting as competitors in the normal protein-protein interactions, the interactions between proteins and nucleic acids, the interactions between proteins and small molecules as well as other intracellular molecular interactions. Peptides having a large number of applications of use, such as therapeutic or diagnostic reagents, may thus be identified without any prior information on the structure of the expected ligand or receptor.

Advances in molecular biology make possible the construction of extremely large collections of peptide sequences as potential inhibitors of the cell cycle and other biological pathways. The generation of large numbers of peptide sequences by the cloning and expression of randomly-generated mixtures is possible in the appropriate recombinant vectors (Oliphant et al. (1986), Gene 44:177–183). Such a large number of peptides can be produced, however, that methods for efficient physical and genetic selection are required. Without flexible methods of analysis, the usefulness of these large peptide libraries in identifying molecules of interest may be lost.

A number of systems for screening proteins and polypeptides have been described. The fusion phage approach can be used to screen proteins (Parmley and Smith, (1988), Gene 73:305–318). Others have described phage-based systems in which the peptide is fused to the pIII coat protein of filamentous phage (Scott and Smith, (1990), Science 249:386–390; Devlin et al., (1990), Science 249:404–406; and Cwirla et al., (1990), Proc. Natl. Acad. Sci. USA 87:6378–6382). Others have also devised combinatorial libraries in other systems. Colas et al. describes the expression of a combinatorial library of peptides displayed in the active loop of E. Coli thioredoxin and the use of a two-hybrid system to select those that bind human Cdk2 (Colas et al., (1996), Nature 380:548–560).

While this art is well developed, a need remains for methods of constructing and screening macromolecule libraries, in addition to those described in the art. For example, the screening methods of this art are limited to and involve the use of assays such as peptides fused to biologically active carrier proteins or fusion proteins compatible with the specific biological activities. In addition, the above methods are limited in that they do not provide flexibility in using macromolecules that can be expressed and genetically selected intracellularly; yet such peptides would add great diversity to the proteins and processes that may be targeted by such libraries.

In contrast to the prior art, novel macromolecule libraries and strategies for identifying peptide inhibitors of cell cycle control and other biological pathways and the targets they inhibit are described herein. The power of this technology is fourfold: it requires no prior assumptions about the biochemical nature of the target pathway; it identifies those members of a pathway that are targets for inhibition by small molecules; weak initial inhibitors can be evolved by mutation and selection into potent inhibitors; and information from this process provides valuable structure-function information to assist in peptidomimetic chemistry to produce drugs directed against cancer and other diseases.

Cancer therapy attempts to kill tumor cells while sparing normal cells. Current therapies use agents that are broadly toxic to dividing cells, make patients profoundly ill, and are only effective against a minority of cancers. Over the last 10 years, three important findings have dramatically improved prospects for more effective chemotherapy. First, cancer is now understood to be a very diverse disease, with different patterns of genetic alterations in different tumors. Second, all cancers show enormous genetic instability due to lesions in the fundamental processes of DNA replication, DNA repair and chromosome segregation; or inactivation of the cell cycle checkpoints that coordinate the events of the cell cycle with each other. Third, the DNA repair, DNA replication, chromosome segregation, and checkpoint pathways have been conserved during evolution, meaning that conclusions from work on simple eukaryotes are directly applicable to humans. It is now possible to exploit these advances by using cells such as budding yeast to launch novel programs of drug discovery that find agents which selectively kill tumors with specific molecular lesions, and have low toxicity towards normal cells.

SUMMARY OF THE INVENTION

The present invention provides methods for generating and screening via genetic selection random libraries of macromolecules to identify sequences that interact with target molecules of interest. The libraries described herein include peptide chimeras (also referred to herein as a peptide library), wherein an amino acid sequence is inserted into a carrier molecule, e.g., a protein backbone. The macromolecules so identified (chimeras or the peptide portion of the chimeras) can be used for therapeutic, diagnostic and related purposes by interacting with a target protein of interest to inhibit or promote the biological activity of that protein. The chimeras can also be used to identify the targets to which they bind, thus providing important information for the development of small molecule inhibitors of the same targets.

The invention further provides a screening method which comprises the steps of (a) growing the host cells under conditions which genetically select for clones that contain peptides that have the ability to disrupt the interactions between molecules that affects a biological process and (b) isolating the vectors that encode the genetically selected peptides. By repeating the affinity selection process one or more times, the plasmids encoding the peptides of interest can be enriched. By increasing the stringency of the selection, e.g., by decreasing the expression of the chimeras, increasing the temperature or varying other medium conditions, peptides of increasingly higher affinity can be identified.

The invention also concerns methods wherein peptides of interest can be mutagenized to create inhibitors of varying affinities. The invention further concerns methods wherein a biological target of the peptide inhibitor can be identified. For inhibitors specific to well characterized pathways, the overexpression of specific members of the pathways can be used to overcome the inhibition and thereby identify the peptide target.

BRIEF DESCRIPTION OF THE DRAWINGS

FIG. 1A shows the amino acid sequence of the *Staphylococcus aureus* native nuclease protein in its precursor form. The underlined portion represents the leader sequence SEQ ID NO:2.

FIG. 1B shows the amino acid sequence of the *Staphylococcus aureus* native nuclease protein in its processed form SEQ ID NO:3.

FIG. 2A shows the amino acid sequence of the *Staphylococcus aureus* nuclease protein, which has been engineered for expression in the disclosed invention. The 5' underlined sequence represents the represents the hemaglutinin epitope. The double underlined sequence represents the solvent accessible surface loop. The 3' underlined sequence represents the polyhistidine tag SEQ ID NO:4.

FIG. 2B shows the amino acid sequence within the engineered *Staphylococcus aureus* nuclease protein that is the hemaglutinin epitope SEQ ID NO:5.

FIG. 2C shows the amino acid sequence within the engineered *Staphylococcus aureus* nuclease protein that is the solvent accessible surface loop into which peptides can be inserted (SEQ ID NO:6).

FIG. 2D shows the amino acid sequence within the engineered *Staphylococcus aureus* nuclease protein that is the polyhistidine tag SEQ ID NO:7.

FIG. 3A shows the nucleic acid sequence of plasmid PSF248 SEQ ID NO:8.

FIG. 3B shows the location of various elements on the PSF248 plasmid SEQ ID NO:9.

FIG. 4 shows the nucleic acid sequence of the PSF248 plasmid after cleavage with BamH1 and re-ligation (for bacterial expression).

FIG. 5A shows the amino acid sequence of the *Staphylococcus aureus* nuclease protein that has been engineered for bacterial expression. The underlined sequence represents the leader sequence for periplasmic expression in bacteria SEQ ID NO:10.

FIG. 5B shows the amino acid leader sequence of the *Staphylococcus aureus* nuclease protein that facilitates periplasmic expression in bacteria SEQ ID NO:11.

FIG. 6 shows the oligonucleotide sequences from the cAMP-dependent protein kinase inhibitory peptide (PKI) loop SEQ ID NO:12; SEQ ID NO:13.

FIG. 7 shows the oligonucleotide sequences from the cAMP-dependent protein kinase non-inhibitory (PKN) loop SEQ ID NO:14; SEQ ID NO:15.

FIG. 8A shows the cAMP-dependent protein kinase inhibitory peptide (PKI) sequence SEQ ID NO:16.

FIG. 8B shows the cAMP-dependent protein kinase non-inhibitory control peptide (PKN) sequence SEQ ID NO:17.

FIG. 9 shows the autophosphorylation sequence from BCY1, a known cAMP-dependent protein kinase substrate sequence SEQ ID NO:18.

DETAILED DESCRIPTION OF THE INVENTION

Definitions

Figure 10:
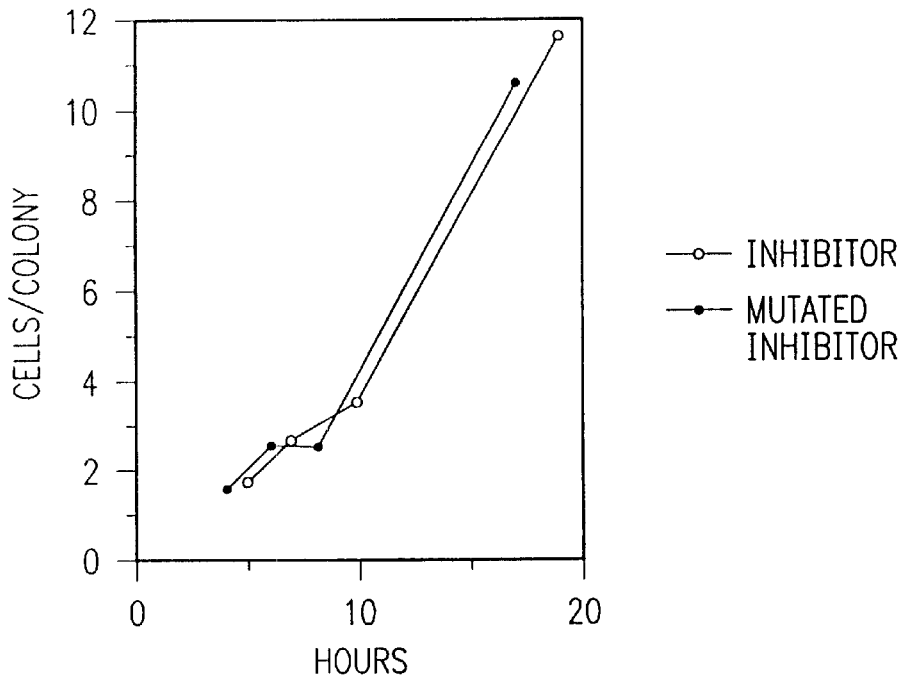
FIG. 10 shows line graphs of budding yeast proliferation under conditions in which nuclease-inhibitory peptide chimera is not expressed (glucose containing medium).

As used in this application, the following words or phrases have the meanings specified.

As used herein, "genetic selection" is defined as a process which identifies the presence of a macromolecule whose in vivo expression inhibits or activates an endogenous cellular process or a pathway or pathways therein and therefore mimics the phenotype caused by genetic activation of its molecular target.

As used herein, "disrupts a biological process," means the inhibition or activation of any biological-signalling pathway whose phenotype can be detected by procedures known in the art.

In order that the invention described may be more fully understood, the following description is set forth.

The present invention provides methods for discovering a macromolecule that disrupts a biological process in a cell. The methods entail a number of steps as follows.

The first step involves generating a gene which encodes a macromolecule a portion of which comprises a randomly generated nucleic acid sequence from a panel of randomly generated nucleic acid sequences (also referred to herein as a peptide library). The peptide library of the invention can be constructed so it is expressed as a portion of a biologically inert carrier protein. In the transfected cells, the expression of the chimeric protein can be placed under the control of either strong inducible promoters such as PGK1 or inducible promoters such as CUP 1 or GAL1 (Naken et al., (1996) Gene 175, 253–260, Wardel et al., (1994), Yeast 10(4):441–449).

The second step in the disclosed method entails transfecting cells (e.g., bacterial cells) with the DNA encoding the chimeric protein and growing them under conditions which allow the intracellular expression of the chimera. The engineered gene is carried on a shuttle vector that affords high intracellular expression in genetically engineered strains of a yeast, e.g., *Saccharomyces cerevisiae*. In different embodiments, the chimera can be expressed from either constitutive or regulated promoters.

The next step involves genetic selection to determine whether the macromolecule so produced disrupts a particular biological process inside of the cell. Any macromolecule that disrupts the biological process can be isolated and characterized, so long as methods for detecting the disruption are known.

In accordance with the practice of the invention, a macromolecule identified by genetic selection would comprise a biologically active small molecule or peptide (or multiples thereof) attached, e.g., covalently attached, to a carrier molecule, e.g., a protein molecule. The carrier molecule can be any molecule that will present the small molecule or peptide to its target process or pathway or pathways therein and does not interfere with the presentation of the small molecule to its target. A preferred carrier molecule is a protein molecule. Others include, but are not limited to, glycoproteins or carbohydrate molecules.

The small molecule can be biological or chemical in nature. In embodiments wherein the macromolecule comprises a peptide, the peptide can be in a range from four to 16 amino acids. Alternatively, the peptide can be shorter or longer than the range.

In embodiments wherein the macromolecule comprises a small organic molecule, the biologically active portion of the molecule can be systematically modified using for example combinatorial chemistry and screened in accordance with the methods of the invention.

In one embodiment of the invention, the peptide library can be presented in a constrained fashion by displaying it from the surface loop of a catalytically inactivated carrier protein. For example, the carrier protein can be a derivative of *staphylococcal nuclease,* a small, heat stable protein, which can be expressed intracellularly at high levels in both budding yeast and bacteria. In addition to the *staphylococcal nuclease,* other well known carrier protein (also referred to herein as fusion protein) systems such as glutathione-s-sythetase-transferase, maltose binding protein or protein A may be used (See Current Protocols in Molecular Biology, (1995) John Wiley & Sons). Moreover, these fusion or carrier proteins can be modified by the addition of an exogenous sequence that facilitates their isolation and purification. These sequences can include a c-terminal polyhistidine sequence and an n-terminal hemaglutinin tag (Moore et al., (1994) P.N.A.S. 91(5), 1843–1847; Chen et al., (1993), P.N.A.S. 90(14):6508–6512).

The libraries of the peptide chimeras can be generated by inserting randomized oligonucleotides encoding for example approximately 6 to 25 amino acids into the gene that encodes the chimeric molecule, e.g,. protein molecule. Random oligonucleotides to generate these libraries can be made by several methods including, but not limited to, split batch synthesis. These oligonucleotides can be synthesized with different restriction sites on either end so that they can be unidirectionally cloned into a chosen sight of the chimeric protein. In one embodiment, these oligonucleotides have EcoRI and XhoI sites which allows them to be cloned into the EcoRI-XhoI site of the vector shown in FIG. 3A.

Once the random libraries are inserted into an exposed loop on the surface of a carrier protein such as *staphylococcal nuclease,* the DNA can be transformed into bacteria where plasmids with these oligonucleotides can be selected and amplified. In one embodiment, the vectors are transformed into a budding yeast cell where the peptide chimeras (one embodiment of the macromolecule of the invention) can be expressed from a yeast specific promoter. The resultant library of clones can then be placed under conditions that allow clones of interest to be genetically selected for the inhibition of a process of interest.

The genetic selection entails growing clones transfected with the vector library under conditions in which a cell expressing a sequence of interest is conferred differential growth characteristics. These differential growth characteristics allow clones of interest to be identified and isolated from the library background. As discussed below, a wide variety of differential growth conditions are well known in the art and can be readily applied to the methods described herein.

To facilitate further characterization of clones of interest, the shuttle vector can be constructed in an embodiment such that a simple restriction enzyme digestion and religation can convert any member of the library to a form that allows high level bacterial expression and one step purification of the peptide chimeras. Such a concentrated and purified peptide clone may then be readily used for a wide variety of biochemical assays.

The expression vector for the peptide chimeras can be modified so that libraries can be sequentially expressed in three ways: on the surface of bacteriophage m13, at high levels inside yeast cells, and as a periplasmic bacterial protein that can be easily purified to homogeneity. This modification can be accomplished by inserting a DNA fragment containing the M13 replication origin and the M13 coat protein downstream of the PGK1 promoter and in frame with the peptide chimera (McLafferty et al., (1993), Gene 128(1):29–36). This insertion can be flanked by sites for Cre, the P1 site-specific recombinase (Hoess et al., (1979) P.N.A.S., 79:3398–3402). Transforming a library in a vector into a bacterial strain that expresses M13 helper functions can produce a phage library in which each member expresses a different library member on its surface. Members of the library that bind to the target protein can be identified in several rounds of selection for binding into the target in vitro. The selected phage can be converted into plasmids suitable for expression in yeast by transforming them into a bacterial strain expressing Cre, leading to the excision of the M13 origin and coat protein gene and repositioning the PGK1 promoter directly upstream of the chimera. These plasmids can then be introduced into yeast to see if expression will mimic the phenotype of mutations in the target gene.

The illustrative example vectors are by no means limiting as the methods and vectors described herein can be easily modified to permit expression of chimeric peptides in other microorganisms, animal cells, or plant cells and vectors well known in the art can be readily modified for use in this system. (For illustrative transfection and expression techniques, See Current Protocols in Molecular Biology, (1995) John Wiley & Sons).

To overcome some of the obstacles inherent in these types of libraries, a number of steps to maximize the sensitivity of the methods described herein are described below. These methods can enhance the outcome of the critical first step in any discovery strategy that is the identification of the inhibitory compounds. These are particularly useful considering the limitations inherent in the art of peptide inhibitors where a given library only explores a small fraction of sequence space: there are $4 \times 10^{15}$ possible 12 amino acid sequences, but it is only possible to isolate $10^8$–$10^9$ yeast transformants.

One way to optimize the use of the disclosed methods is to maximize peptide chimeras expression by using a strong constitutive promoter such as PGK1 on a high copy, 2 $\mu$m-based vector and optimizing the codon usage of the chimeras (Moekma et al., (1987) Mol Cell Bio 7, 2914–2924, Lee et al., (1988), Biochemistry 27:5101–5107). Although inducible promoters offer a wider variety of genetic selections, they are expressed at substantially lower levels than the strongest constitutive promoters. Additionally we can regulate expression from the constitutive promoter by engineering binding sites for Mat α 2, a transcriptional repressor, into the PGK1 promoter, and expressing Mat α2 from the inducible CUP1 promoter (Johnson and Herskowitz (1985), Cell 42, 237–247; Ward et al. (1994), Yeast 10, 441–449; Cooper et al., (1994), Gene and Development 8(12):1400–1410).

Another way to maximize the potential of the described methods and peptide libraries is to use a defined, sensitive assay for technology development. A primary goal in this art is to select inhibitors of biological pathways. To effect this goal, peptide inhibitors can be assayed for their effect on a defined protein interaction. A version of the two-hybrid interaction has been described in which the interaction between two proteins induces the expression of the URA3 gene (Vidal et al P.N.A.S. 1996 93:1031520). Because expression of this gene can be selected against by growing cells on medium containing 5 fluoroorotic acid, inhibition of the two hybrid interaction confers a growth advantage on this medium, making it possible to select those members of a protein-peptide chimera library that inhibit a characterized protein- protein interaction.

In a specific embodiment of this method, the macromolecules are inhibitors of the interaction between the Retinoblastoma protein and the Dp1 transcription factor (Vidal et al. (1996), P.N.A.S. 93:10315–10320). Methods for evaluating protein-protein interaction such as the yeast two-hybrid system are well known in the art and are readily applied to the disclosed methods. In this Retinoblastoma-Dp1 system, the interaction is known to depend on a defined 20 amino acid stretch of Dp1. Therefore, using this knowledge, a modified version of the disclosed methods used in conjunction with the two-hybrid system can be utilized to select peptide variants of the DP1 or Retinoblastoma molecules that that cause inhibition of this interaction.

Another way to maximize the potential of the disclosed protocols is to use multiple rounds of selection to isolate weak inhibitors. In many cases, initial inhibitors may only provide a partial inhibition of their target. But as long as this partial inhibition produces a growth advantage, multiple rounds of selection can isolate the inhibitor. For example, if a genetic selection gives a particular peptide chimeras a 100-fold growth advantage over the other library members, the transformant harboring this chimera can be enriched 100-fold over other library members.

By isolating plasmid DNA from the pooled transformants, this enrichment is maintained, and the inhibitor-encoding plasmid is separated from any chromosomal mutations that could confer a growth advantage. The pooled DNA can be amplified in bacteria, retransformed into yeast and the selection can be applied again producing another round of enrichment. This approach can isolate inhibitors that confer only mild growth advantages: an inhibitor that confers a 100-fold growth advantage can be isolated from a library of $10^8$ potential inhibitors by four rounds of selection.

Yet another way to enhance this technology is by using methods for mutagenizing weak inhibitors into strong ones. Specifically, we can mutagenize a peptide encoding a sequence of a weak inhibitor and using error prone-PCR with primers that immediately flank the peptide sequence we can then insert it in unmodified vector DNA (Burke et al., (1996) Nucleic Acids Research 264:650–666). Multiple rounds of amplification in the presence of base analogs can produce multiple amino acid substitutions in the peptide. The PCR product can be digested and ligated into the peptide-nuclease vector, to create a pool of mutagenized plasmids from which stronger inhibitors can be selected.

Utilizing the methods described herein, we can identify the targets of any peptide inhibitor that is identified, a key to successful drug discovery. Specifically, we can use at least three strategies to identify targets of peptide chimeras. The first entails relieving inhibition by overexpressing the target protein. The second entails using the two-hybrid system to isolate proteins that bind that peptide (Fields, S. and Song, O. (1989), Nature 340:245–246). The third is co-purification of the protein target and its peptide inhibitor, using affinity tags on the inhibitor, followed by target identification by mass spectrometry (Yates et al., (1996) Analyst 121:65R–75R).

Since peptide inhibitors act as stoichiometric inhibitors of their targets, increasing target expression should overcome the inhibitor. For this purpose, the initial clones identified in the inhibitor peptide libraries, which are likely to confer weak inhibition, can provide maximal sensitivity to target overexpression. In pathways where members are well defined, such as those which are activated by pheromones, DNA damage, or spindle defects, the expression of individual members can be increased and effects on the peptide inhibition can be observed. In this way, the specific targets in these well-defined pathways can be identified.

Another way in which targets of peptides can be identified is through the use of a two-hybrid system in which the interaction of two proteins drives a reporter gene (Fields, S. and Song, O. (1989), Nature 340:245–246). As an example of the utility of this two-hybrid system, the disclosed methods can be used to isolate proteins that bind to the peptide by expressing peptide inhibitors fused to the DNA-binding domain of GAL4. This peptide-GAL-4 fusion protein chimera can be used to screen libraries of yeast genes fused to a transcriptional activation domain for their ability to activate transcription from the GAL1 promoter (Fields, S. and Song, O. (1989), Nature 340:245–246).

The specific chimeric libraries and methods of their use and enhancement are in no way limiting, as there are a variety of possible modifications of this invention. For example, in a variant of the disclosed two-hybrid screen, a transcriptional activation domain can be fused to the peptide and the target protein is selected from a library of proteins that are fused to a DNA-binding domain. In this way, libraries of chimeras can be selected to identify members that can induce transcription of a target gene whose promoter contains a binding site for the DNA-binding domain.

The flexibility of the methods described herein allows for modifications of the invention. In particular, the general screening methods allow a wide variety of alternative ways to identify chimeras of interest.

General selection techniques may be modified and rearranged to evaluate any biological pathway of interest. For example, inhibitors of a pathway can be selected when the inhibition of that pathway either allows inhibited cells to proliferate under conditions where uninhibited cells fail to proliferate, or allows inhibited cells to survive under conditions where uninhibited cells die. Conversely, inhibitors of a pathway can be selected when inhibition of that pathway either prevents inhibited cells from proliferating under conditions where uninhibited cells do proliferate, or where inhibited cells die and uninhibited cells survive.

A general embodiment is a selection for protein-peptide inhibitors that arrest the cell cycle. For example, cells that have mutations in the MEC1 gene, cannot arrest their cell cycle in response to inhibition of DNA replication. As a result, treating cycling mec1 mutant cells with hydroxyurea (an inhibitor of DNA replication) causes them to die rapidly. In contrast, if these cells are arrested in mitosis or the G1 phase of the cell cycle, not attempt to replicate their DNA and therefore do not die when exposed to hydroxyurea. This method provides at least a 100-fold enrichment for arrested cells.

By using a conditional promoter, such as the GAL1 promoter to control expression of the protein-peptide chimera, this method can be used to enrich those protein-peptide chimeras that arrest the cell cycle by any mechanism, including but not limited to, inhibition of the cell cycle machinery, activation of cell cycle checkpoints, mimicking signals generated by nutrient starvation, and inhibiting the synthesis of amino acids and other secondary metabolites required for progress through the cell cycle.

If a biological pathway induces gene transcription of target genes, the expression of these genes can be rendered toxic by fusing their promoter to a gene that encodes an inhibitor of cell proliferation (such as an inhibitor of a cyclin dependent kinase (Morgan, D. O. (1995) Nature 374:131–134.), or a protein that kills cells (such as diphtheria toxin). In addition, it would be possible to select inhibitors of the pathways that cause exposure to galactose to induce the GAL1 promoter by fusing this promoter to the SIC1 gene whose high level expression prevents cell proliferation (Mendenhall, M. D. (1993), Science 259:216–219).

By transforming such cells with a library of protein-peptide chimeras and selecting for those cells that can grow on medium that contains galactose plus ethanol, it is possible to select chimeras that inhibit the induction of the GAL1 promoter. Since almost all biological pathways produce transcriptional responses, it is possible to design similar selections for the inhibition of any pathway of interest.

In addition, these methods provide for alternative means of target identification. The sequencing of the entire yeast genome has made it possible to determine protein identity from less than 100 fmol of protein by mass spectrometry, even when the sample is a mixture of many proteins (Yates et al. Analyst, 1996 Jul, 121(7):65R–76R). Since the protein-peptide chimeras contain affinity tags, these tags can be used to isolate complexes between an inhibitory protein-peptide chimera and its target from a crude cell extract. Target proteins can be identified as proteins that are present in the affinity purified material from cells that express the inhibitor, but are absent from affinity purified material prepared from control cells that do not express the inhibitor.

ADVANTAGES OF THE INVENTION

The disclosed genetic screening method offers many advantages over those of the prior art. In particular, this screening does not require a detailed biochemical understanding of the pathway and can provide inhibitors of several different steps of the same pathway. This screening entails the step of growing the host cells under a specified set of conditions that genetically select for clones that contain peptides that have the ability to affect the interactions between biologically important molecules.

The peptide library and methods described herein have a number of advantages over the prior art. In the peptide chimera embodiment, by presenting a peptide that is constrained by its placement in the surface loop of a carrier protein, a library of peptides is produced containing peptides that are more conformationally restricted and can interact with their binding partners with higher affinity than is observed for unconstrained peptides (McLaffery et al., Gene 128 (1993), 29–36, Oldenburg et al., P.N.A.S. 89 (1992) :5393–5397).

The intracellular expression of the conformationally constrained peptide library provides advantages over the prior art in that the peptide library has a wide access to a diverse number of intracellular targets. In this manner, the members of this library have the potential to interact with a wide variety of molecules involved in growth and regulatory processes within the cell.

Unlike the libraries disclosed in the prior art, the construction of this peptide library allows the sequences of interest to be easily modified and manipulated. By repeating the affinity selection process one or more times, peptides of interest can be enriched. By increasing the stringency of the selection, e.g., by increasing the temperature or other medium conditions, peptides of increasingly higher affinity can be identified. By manipulating the sequence of a peptide of interest via the use of the disclosed procedures such as error prone PCR, variants with altered biological activity can be generated, isolated and characterized.

The following examples are presented to illustrate the present invention and to assist one of ordinary skill in making and using the same. The examples are not intended in any way to otherwise limit the scope of the invention.

EXAMPLE 1

A peptide chimera was generated that presents a 22 amino acid inhibitory peptide directed against cAMP-dependent protein kinase and inhibits the growth of budding yeast by inhibiting this kinase. In addition, the purified peptide chimera (i.e., peptide-nuclease) inhibits pure cAMP-dependent protein kinase in vitro.

In this example, an oligonucleotide encoding a 22 amino acid peptide is synthesized which is reported to inhibit cAMP-dependant protein kinase with nM affinity (FIG. 8A). As a control, a non-inhibitory peptide chimera was also constructed. The oligonucleotide sequences encoding these peptides were constructed to incorporate Eco-R1 and XhoI sequences to facilitate its unidirectional cloning (see FIGS. 6 and 7).

The oligonucleotide clones were ligated into the external loop of an engineered *Staphylococcus aureus* nuclease coding region of the gel purified pSF248 plasmid which had been digested EcoRI-XhoI, following procedures described in Maniatis et al., Molecular Cloning, a Laboratory Manual, (1989), Cold Spring Harbor Laboratory Press. (See FIG. 4). As shown in FIGS. 2A and 2C, the fusion protein (peptide chimera) backbone has been engineered for easy use and includes an HA tag, and a polyhistidine stretch. In yeast pSF248 expresses the peptide-nuclease chimera under the control of the GAL1 promoter.

The above ligation mixture was transformed into bacterial strains SE6004 (r+m+Ñ lacU169 araD139 relA strR thi-lamB560 prlA4) or TG1 and selected on ampicillin. Individual colonies were isolated, sequenced (Maniatis et al., Molecular Cloning, a Laboratory Manual, (1989), Cold Spring Harbor Laboratory Press) to verify the reading frame, and plasmids were prepared following procedures described in Maniatis et al., Molecular Cloning, a Laboratory Manual, (1989), Cold Spring Harbor Laboratory Press.

Plasmids containing the 22 amino acid peptide were transformed into the LL8 yeast strain (derived from SP1, Toda et al., (1987) Cell 50, 277–284) which expresses human cAMP-dependent protein kinase and has deletions in three genes encoding catalytic subunits of yeast cAMP-dependent protein kinase (TPK1, TPK2, TPK3) and expresses the human cAMP-dependent protein kinase and selected for growth on medium lacking uracil using published transformation protocols (Ito, H., Fukuda, Y., Murata, K. and Kimura, A. (1983). Transformation of Intact Yeast Cells Treated with Alkali Cations. J Bacteriol 153, 163–168.)

For optimal expression of the inducible peptide chimeras, yeast strains were grown in synthetic media with 2% galactose and lacking uracil prepared as described in Sherman, F., Fink, G. and Lawrence, C. (1974). Methods in Yeast Genetics, Cold Spring Harbor Laboratory Press. Plasmids from yeast strains of interest were recovered as described in Guthrie, C. and Fink, G., Guide to Yeast Genetics and Molecular Biology, Methods in Enzymol., vol. 194.

Figure 11:
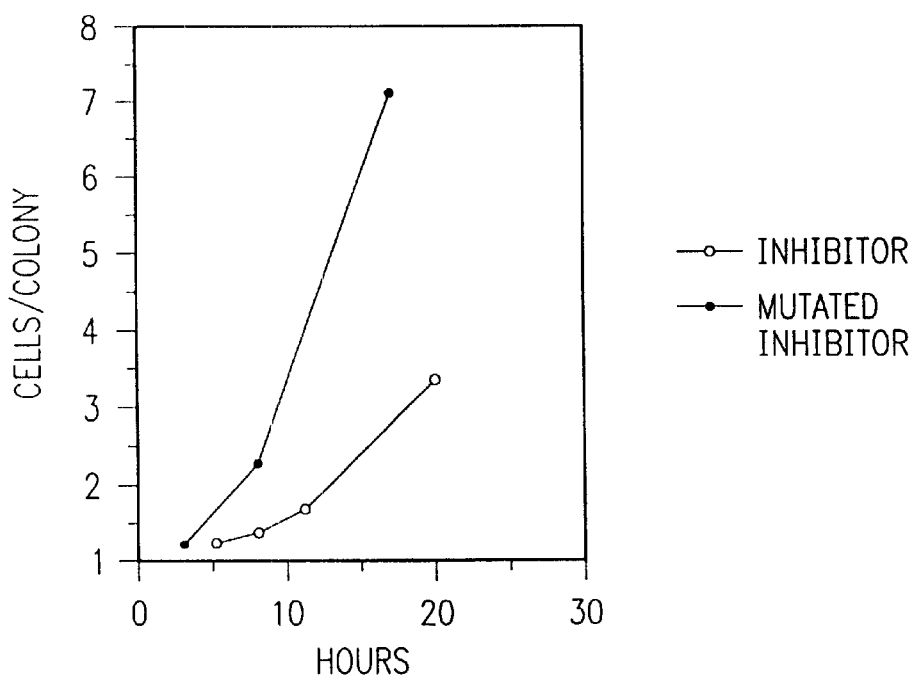
FIG. 11 shows line graphs of budding yeast proliferation under conditions in which nuclease-inhibitory peptide chimera is expressed (glucose containing medium).

The genetic selection in this protocol entailed an analysis of growth on glucose and galactose-containing medium, wherein the growth of individual cells was quantified over time by counting the number of cells in cell colonies. This data was compared to data generated under identical conditions from a control peptide-nuclease chimera (PKN loop) that carries a mutant version of peptide that fails to inhibit cAMP-dependent protein kinase (see FIGS. 10 and 11). As shown in FIGS. 10 and 11, the presence of the inhibitory peptide chimera (PKI loop) produces a marked difference in yeast growth patterns.

Figure 12:
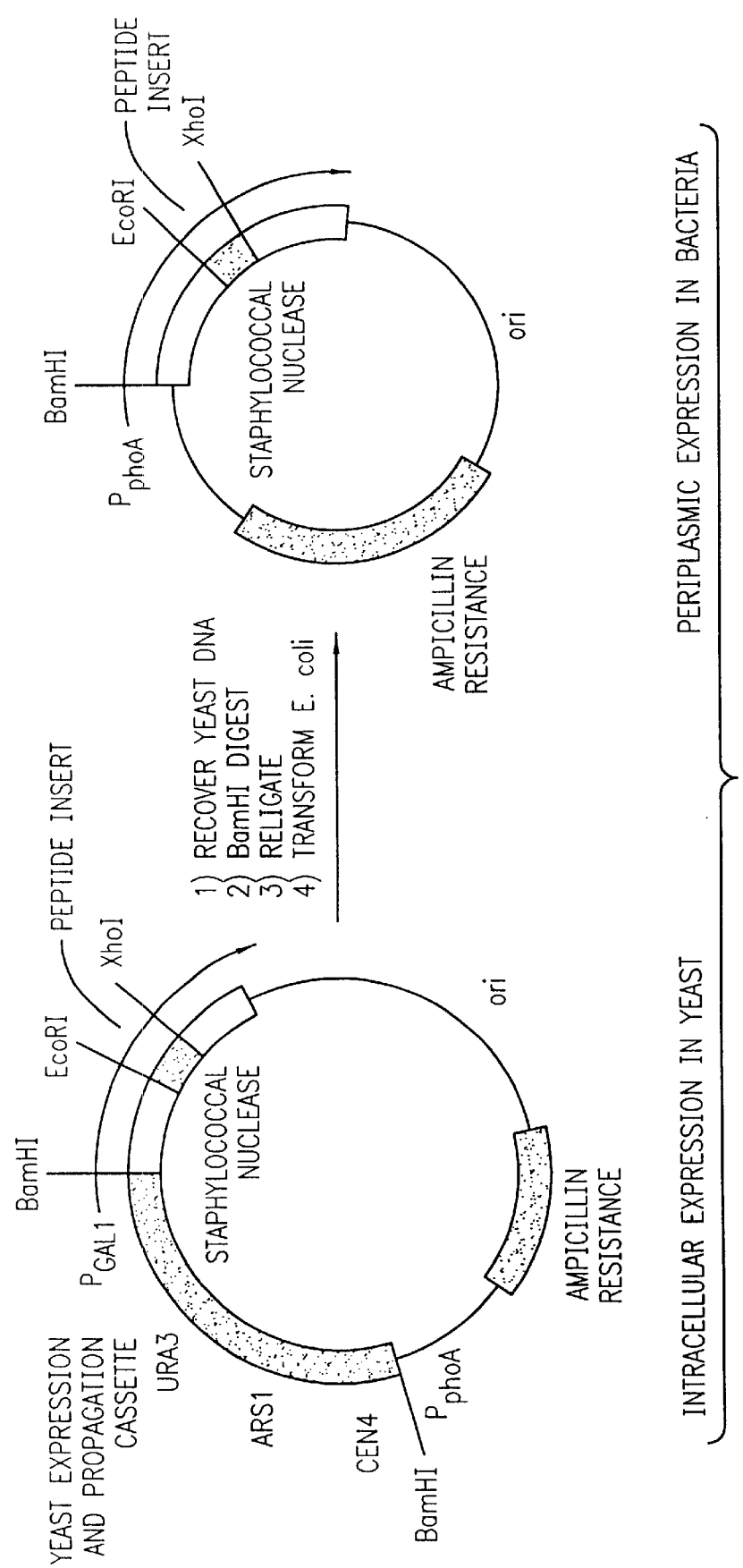
FIG. 12 are schematics of the PFS248 plasmid, which show the changes that result from the BamH1 cloning step (which facilitates expression in bacteria).

Protein for in vitro studies was expressed in bacteria and purified. In this procedure, the pSF248-PKN plasmid was cut with the restriction endonuclease and BamHI and religated in order to allow efficient bacterial expression of the peptide chimera. As shown in FIG. 12, this digestion allows the conversion from yeast to bacterial expression via removal of yeast promoter, yeast selectable marker, yeast replication origin, and HA epitope. This digestion and re-ligation also leads to the juxtaposition of PhoA promoter and leader sequence with nuclease coding sequence so that they are now immediately 5' to the fusion protein.

The Bam-H1 cut and re-ligated plasmid was transformed into bacterial strain SE6004 and a chimeric protein preparation was generated via the periplasmic protein preparation methods described in Current Protocols in Molecular Biology, (1995) John Wiley & Sons. In this system, high expression results from growth on low phosphate medium and periplasmic extraction occurs. The peptide-nuclease chimeras from the periplasmic protein preparation were then purified by metal affinity chromatography (Moore et al., (1994) P.N.A.S. 91(5):1843–1847).

An in vitro analysis of the properties of the peptide chimera was undertaken wherein the biochemical inhibition of cAMP-dependent protein kinase was evaluated in vitro. In this procedure, the effects of purified peptide-nuclease chimeras were assayed for their ability to inhibit cAMP dependent protein kinase phosphorylation of the control substrate autophosphorylation sequence from BCY1 (FIG. 9).

Figure 13:
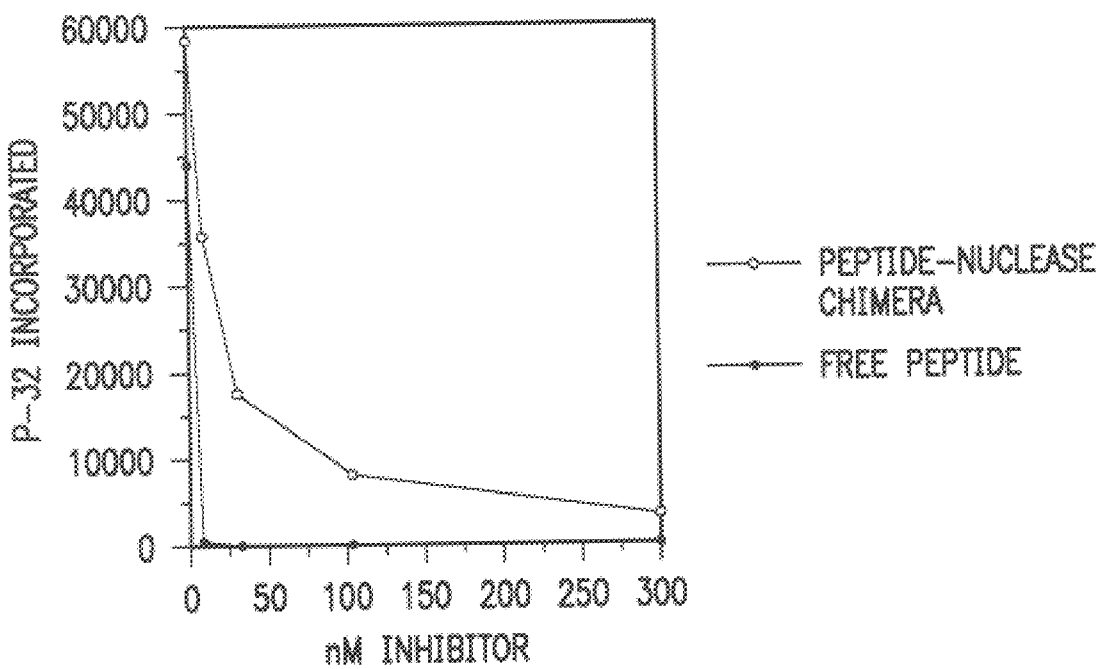
FIG. 13 shows line graphs of in vitro cyclic AMP-dependent protein kinase inhibition by a purified recombinant *staphylococcal nuclease* inhibitor chimera.

The chimeras, kinase and substrate were evaluated in a reaction buffer containing 50 mM HEPES, 1 mM EGTA, 10% glycerol, 1 mM DTT, 1 mM MgCl2, and 0.4 mg/ml BSA (to stabilize the kinase) and 1 mM PMSF. The enzyme concentration in this buffer was 0.005 uM. Reactions were started with 10 minute preincubation with either the PKI chimeric inhibitor or the PKN control chimera. PKI concentration ranged from 3 uM to 0.03 uM in three-fold dilutions. Substrate was added at 2 uM along with ATP (100 uM ATP, 1.5 uci/reaction γATP). Reactions were incubated at 30 degrees centigrade for 3, 10 or 30 minutes. Reactions were then quenched with protein loading buffer, and run on SDS gel (Current Protocols in Molecular Biology (1995), John Wiley & Sons). The inhibitory effects of the chimeric peptides on the reaction were observed by monitoring the differential 32P incorporation into the BCY1 substrate by gel electrophoresis (FIG. 13).

EXAMPLE 2

As described in this example, the libraries and methods disclosed herein may be manipulated in a number of ways. While this example demonstrates the presentation of a library of random peptides exposed on a surface loop of an engineered variant of *staphylococcal nuclease,* a small, heat-stable protein is discussed, other proteins are possible such as phosphoglycerate kinase (Mas et al., (1988), Proteins 4, 56–62), barnase (Sali et al., (1988), Nature 335, 740–743) or single chain antibodies (Laroche et al., (1991), J. Biol. Chem. 266:16343–16349). The nuclease variant is catalytically inactive and presents the peptides in place of a surface loop which is disordered in the native structure but whose base is well-characterized structurally (Cotton et al, (1979) P.N.A.S. 76:2551–2555)(FIG. 2). The library of peptides can consist of entirely random sequences. Alternatively, specialized libraries can comprise a set of heavily mutagenized derivatives of an initial peptide sequence, chosen because it mediates a protein-protein interaction that is the target of inhibition (Oliphant et al., (1989) P.N.A.S. 86:9094–9098).

Libraries are prepared by the insertion of short EcoRI-XhoI DNA fragments into EcoRI-XhoI cut vector DNA. The EcoRI-XhoI fragments are prepared by mutually primed synthesis from chemically synthesized oligonucleotides. For fully random libraries, nucleotides that encode the central amino acids of the peptide are fully randomized. Oligonucleotides used to create libraries based on a starting peptide sequence are made by several methods including, but not limited to, synthesis with doped nucleotides, and split-batch synthesis (Oliphant et al., (1989) P.N.A.S. 86, 9094–9098; Current Protocols in Molecular Biology (1995), John Wiley & Sons).

In the split batch synthesis method, the oligonucleotide synthesis matrix is split in two, prior to synthesis of each codon. One half receives a nucleotides corresponding to the starting sequence and the other half receives all four nucleotides. Before synthesis of the next codon, the two halves of the matrix are mixed together and then split again. This can generate a library of sequences in which the original peptide sequence is present at (approximately) 50% in each position and all other codons are present at (approximately) 50%. It allows the search for inhibitors to be biased toward sequences that are derived from the regions of proteins known to interact, and thereby potentially reduces the number of peptides that must be screened to isolate inhibitors.

Each new library is transformed into *E. coli* to generate a pool of at least 108 members. After preparation of plasmid DNA, the library is transformed into yeast, and expression of the chimeric nuclease proteins is induced on galactose-containing medium. Because the nuclease chimera is soluble and small enough to freely diffuse into both the cytoplasm and nucleus, chimeras can inhibit functions in either of these compartments (Alberts et al., (1994), Molecular Biology of the Cell, 3rd Edition, Garland, N.Y.). However, future variants could direct the nuclease specifically to the nucleus or other cellular compartments. Colonies with the desired phenotype are identified (examples presented below) and plasmid DNA recovered. It is then cut with BamHl, re-ligated and transformed into *E. Coli.* High level production of the chimeric nuclease protein is induced by growth in low phosphate medium. Because the *E. coli* version of the nuclease chimera is linked to a short signal sequence, chimeras are expressed in the bacterial periplasm (FIG. 5B). This permits the isolation of large quantities of partially purified chimeric proteins by a simple procedure. Purification to homogeneity is made possible by a C-terminal hexahistidine stretch that allows expressed proteins to be purified by metal chelate chromatography (Current Protocols in Molecular Biology,(1995), John Wiley and Sons).

Effective inhibitor peptides are isolated from the library by selecting genetically for those rare members whose expression produces a phenotype similar to that produced genetically by a loss-of function mutation in the target protein (examples given below). Candidate inhibitors are then expressed in bacteria and purified to homogeneity. The potency of the inhibitor is then determined by direct biochemical measurement in vitro. If necessary, successive rounds of selection are performed to identify inhibitors with progressively higher potency.

Once the chimeric library as described herein is generated, the genetic selection of inhibitors is undertaken in a number of different ways. As described in detail below, this selection includes methods for screening inhibitors of protein activity, inhibitors of functions required for cell cycle Progression, inhibitors of signal transduction pathways and inhibitors of protein-protein interactions.

In the inhibitor screens described below, the details refer to a method designed to identify inhibitors in the budding yeast *Saccharomyces cerevisiae*. This organism was chosen for convenience during the development stage of the method. However, the inhibitor-selection method can be modified to permit the identification of inhibitory peptides in any process in a eukaryotic and prokaryotic organism for which the phenotype of inhibition of the process are scored.

In one method of isolating inhibitors, a yeast-bacterial shuttle vector is made that carries a gene encoding a catalytically inactive *staphylococcal nuclease* variant (Cotton et al, (1979) P.N.A.S. 76, 2551–2555; Sikorski et al., (1989), Genetics 122:19–27). Random peptide sequences are inserted in place of residues 42 to 52 of *staphylococcal nuclease* (FIG. 2C). In wild-type nuclease, these residues form a structurally disordered solvent-accessible surface loop (FIG. 1B). Within the conformationally restricted context of the nuclease chimeras, sequences encoding protein kinase substrates is inserted, and these sequences are phosphorylated in vitro. Thus, peptides present in engineered nuclease chimeras also appear to be solvent-accessible. The engineered nuclease gene are carried on a shuttle vector that directs high level inducible expression in *Saccharomyces cerevisiae*, and, following a cloning step in which the plasmid is cut with BamH1 and then religated, also in *E. coli*.

Libraries of peptide sequences are screened in cells to identify those peptides whose expression inhibits a cellular process and therefore mimics the phenotype caused by genetic inactivation of the process. The only limitation on the range of target proteins that can be inhibited by this approach is the need to identify a set of conditions under which cells that lack a particular process survive, while cells that can still perform it die. Alternatively, a set of conditions is identified under which cells that lack a particular process proliferate, while cells that can still perform it fail to proliferate. A number of examples of such selections follow. These are nonrestrictive and are intended only as a guide to a wide variety of possible selections whose details are determined by the type of inhibitor that is being sought.

Using the described methods, it is also possible to isolate peptides that activate a cellular process under conditions in which this process would not normally be active. The requirement for such selection is that activation of the desired process allows cells to proliferate under a set of conditions in which they would otherwise fail to proliferate, or allow cells to survive under a set of conditions in which they would otherwise die.

The methods disclosed herein can be utilized to screen for inhibitors of functions required for cell cycle progression. Such a screening assay can be useful for identifying potential chemotherapeutic drugs. These inhibitors can be identified by exploiting conditions in which cells progressing through the cell cycle die, whereas those that are arrested survive. This is made possible by mutations in checkpoint controls, such as the mec1 mutation in yeast, which lead to the death of cells that attempt to traverse S-phase in the presence of DNA-synthesis inhibitors. For example, by screening a library of peptides based on a known substrate of the p34 protein kinase (which drives progress through the cell cycle), it is possible to identify inhibitors of p34 based on their ability to allow the survival of mec1 cells in the presence of hydroxyurea (Weinart et al., (1994), Genes & Development 8(6):652–665).

The methods disclosed herein are utilized to screen for inhibitors of signal transduction pathways. It is often possible to devise selections that favor the growth of cells whose signal transduction pathways have been inactivated or inhibited. Three nonlimiting examples follow.

First, treatment of yeast cells with mating factors induces a cell cycle arrest via a signal pathway which includes a G-protein coupled receptor and a number of protein kinases (Whiteway et al., (1995), Science 269:1572–1575). Inhibitors of components of this cascade allow yeast cells to grow in the presence of mating factors. Second, inhibitors can also be selected for pathways that involve cAMP-dependent kinases. Unrestrained activity of cAMP-dependent kinase in yeast prevents cells from sporulating (Matsumoto et al., (1983), Cell 32:417–423). Peptides that inhibit Ras (the G protein that activates cAMP-dependent kinase), the cAMP-dependent kinase, or other proteins required for kinase activation are selected by demanding that cells that contain a constitutively active Ras gene sporulate as a consequence of the presence of a chimera that inhibit Ras, cAMP-dependant kinase or other proteins in this pathway. Third, in mammalian cells the phosphorylation of tyrosine 527 (Y527) of c-Src acts to inhibit activity of the kinase, and src mutants lacking this phosphorylation site cause malignant transformation (Murphy et al., (1993), Molecular & Cellular Biology 13(9):5290–5300). Inhibitors of the kinase that acts on tyrosine 527 could be identified by selecting for variant peptides derived from the sequence around this phosphorylation site whose expression transforms mammalian tissue culture cells, thus allowing them to proliferate in conditions in which normal cells do not proliferate.

The methods described herein can be further modified to create model substrates. Many biochemical assays require the analysis of enzymatic modification of particular residues on a complex protein. It is often difficult to obtain the substrate proteins used in these assays in pure form. In addition, such proteins may have several different sites of modification, making it difficult to monitor modification at a specific sites. Both of these problems can be circumvented by expressing a small fragment of the target protein that contains the desired site of modification as a *staphylococcal nuclease* chimera. This model substrate can be produced in large quantities, easily purified to homogeneity, and used as a substrate in assays for the modifying activity. In example 1, we have produced test substrates for cAMP-dependent protein kinase, by inserting known substrate sites into the nuclease backbone. This chimera can be phosphorylated only by the appropriate protein kinase.

A powerful modification of our method entails the coupling of physical and genetic selections for inhibitory peptides. In this modification, a library of peptides can be screened to identify members that bound to the protein to be inhibited. Such a selection can be used in a wide variety of techniques, including but not limited to, bacteriophage display, bead binding, and translational presentation. The DNA segments encoding those members of the library that bound to the target protein would be transferred en masse to our vector system and then introduced into cells in which inhibition of the target activity could be selected.

Alternatively, our vector system can be modified to permit a preliminary step in which the *staphylococcal nuclease* chimeras would be displayed on the surface of bacterial cells or bacteriophage that can be selected for binding to a target protein. Subsequently, the fraction of the library recovered from those organisms that bound to the target can be transferred into a eukaryotic organism for selection of the subpopulation that encodes inhibitors of the target protein.

EXAMPLE 3

Inhibitors of cell cycle checkpoints are attractive therapeutic agents: an inhibitor of the checkpoint that arrests cells with DNA damage would kill tumors whose genetic instability was due to high levels of spontaneous damage. As described below we can develop specific genetic selections for inhibitors of a wide variety of pathways. Exemplary protocols for representative well known pathways such as the pheromone response pathway, the DNA damage checkpoint pathway and the spindle assembly checkpoint pathway are herein disclosed.

As part of the mating pathway, yeast cells of the α mating type secret a factor, α pheromone that arrests cells of the a mating type in G1 by activating Far1, an inhibitor of G1 cyclin/Cdc2/28 complexes (Tyers, (1996) P.N.A.S. 93(15), 7772–7776). Three aspects of this pathway make it an excellent target for inhibitor development: it is the best characterized eukaryotic signal transduction pathway, a factor, the pheromone that arrests cells of the a mating type is a small, unmodified, water soluble peptide, and varying the concentration of a factor controls the degree of growth inhibition. We can identify the minimal concentration of α factor needed to prevent colony formation by diploid cells that are homozygous for the α mating type (α/α diploids). Using diploid cells minimizes the chance of isolating recessive chromosomal mutations that inactivate the pheromone response pathway.

We can transform these cells with the pools of the peptide chimera library, harvest the transformants from each pool, and plate them on a factor-containing plates. We can harvest all the cells growing on these plates, isolate DNA, amplify it in bacteria, retransform the amplified DNA into yeast, and repeat the selection. We can monitor the enrichment of plasmids encoding peptide inhibitors by determining the fraction of a factor-resistant cells at each round of transformation. Once this ratio reaches 0.25 we can isolate the plasmids from individual a factor-resistant colonies and test them for their ability to confer growth on a factor.

A specific protocol for such a genetic selection entails the following steps. Plate transformants in MATa/MATa bar1/bar1 ura3/ura3 diploid on glucose containing medium that lacks uracil (Current Protocols in Molecular Biology,(1995), John Wiley and Sons). Pool transformants and plate on galactose containing medium that lacks uracil and contains 0.5 ug/ml alpha factor. The genetic selection occurs here because only cells containing peptide inhibitors of the pheromone response pathway or chromosomal mutations in the pathway can grow on galactose containing medium that lacks uracil and contains 0.5 ug/ml alpha factor. Chromosomal mutants can be discriminated against by recovering DNA from the pooled colonies that grew on galactose containing medium that lacks uracil and contains 0.5 ug/ml alpha factor.

At this point, we can transform the recovered mixture into bacteria to isolate the plasmids encoding peptide-nuclease chimeras, then re-transform these isolates into yeast and repeat the selection procedure. Only those plasmids that encode peptide-nuclease chimeras that inhibit the pheromone response pathway will be enriched by this procedure and in this manner clones of interest can be selected.

With the disclosed methods, the DNA damage checkpoint can also be examined. Cells that have a double stranded break in a non-essential chromosome activate the DNA damage checkpoint and arrest in G2 (Sandell, (1993) Cell 75, 729–739; Garvik et al., (1995) Mol Cell Bio 15(11), 6128–6138). If the cells are defective in checkpoint adaptation this arrest is permanent. Genetically inactivating the checkpoint allows the cells to proliferate, thus creating a selection for inhibitors of the damage checkpoint. We can use this selection to find peptide inhibitors of the DNA damage checkpoint. A specific protocol for such a genetic selection entails the following steps. We can plate transformants in a strain containing a non-essential chromosome that carries a site for cleavage by the HO endonuclease (driven by the GAL1 promoter), the rad52 mutation to block repair of double-stranded breaks, and the cdc5-ad mutation (which blocks adaptation to the DNA damage checkpoint) on glucose containing medium that lacks uracil.

At this stage we can then pool transformants and plate them on galactose containing medium that lacks uracil. Genetic selection will occur because only cells containing peptide inhibitors of the damage checkpoint pathway or chromosomal mutations in the pathway can grow on galactose containing medium that lacks uracil.

Chromosomal mutants can then be isolated by recovering DNA from the pooled colonies that grew on galactose containing medium that lacks uracil, transforming this mixture into bacteria to isolate the plasmids encoding peptide-nuclease chimeras, and re-transforming into yeast and repeating the selection procedure. Clones of interest will thereby be selected in this procedure in that only those plasmids that encode peptide-nuclease chimeras that inhibit the damage checkpoint pathway will be enriched.

With the disclosed methods, the spindle assembly checkpoint can also be examined. Overexpressing a kinase in the spindle assembly checkpoint (Mps1) activates the checkpoint and arrests the cell cycle of cells whose spindles are normal (Hardwick et al., (1996) Science 273:953–956). Thus, inhibitors of the checkpoint can be isolated as library members that allow cells overexpressing Mps1 to grow.

A specific protocol for such a genetic selection would entail the following steps. First, plate transformants in a strain containing integrated copies of the MPS 1 gene driven by the GAL1 promoter, and the CDC28-VF mutation (which blocks adaptation to the DNA spindle assembly checkpoint) on glucose containing medium that lacks uracil. Second, pool transformants and plate on galactose containing medium that lacks uracil.

At this point, only cells containing peptide inhibitors of the spindle assembly checkpoint pathway or chromosomal mutations in the pathway can grow on galactose containing medium that lacks uracil. Chromosomal mutants can then be identified by recovering DNA from the pooled colonies that grew on galactose containing medium that lacks uracil, transforming this mixture into bacteria to isolate the plasmids encoding peptide nuclease chimeras, re-transforming into yeast and repeating the selection procedure. Clones of interest will thereby be selected in this procedure in that only those plasmids that encode peptide-nuclease chimeras that inhibit the spindle assembly checkpoint pathway will be enriched by this procedure.

EXAMPLE 4

The system described herein can be used in a novel strategy for isolating highly specific inhibitors of protein kinases. For example, we can exploit knowledge of the phosphorylated residues in p34cdc2 to identify inhibitors of the kinases and phosphatases that catalyze modification at these sites.

With the disclosed system, one can generate competitive kinase inhibitors that are able to block the phosphorylation or dephosphorylation of individual sites on p34cdc2 in vivo. This can be accomplished by inserting an oligonucleotide encoding a short peptide from p34cdc2, a mutagenized library based on the sequence of a phosphorylated peptide from p34cdc2, or a completely random peptide library into the gene of the small, structurally characterized and resilient carrier protein, *staphylococcal nuclease.*

To produce mutagenized versions of peptides that include phosphorylation sites we can use either doped or split synthesis of the peptide-encoding oligonucleotide. During the step entailing oligonucleotide synthesis, each nucleotide can be doped, to varying extents, with variant peptides (Hutchinson, C. A. 3d, Nordeen, S. K. Vogt, K. and Edgell, M. H. (1986). Proc. Nat. Acad. Sci. USA 83, 710–714). It is predicted that among these variants, peptides that mimic high-affinity kinase substrates can be found and that, when expressed in cells as part of chimeric proteins, these peptides can act as competitive inhibitors of the enzymes that phosphorylate p34cdc2. Effective inhibitors can be isolated from the pool of chimeras by selecting genetically for those rare proteins whose expression interferes with the function of kinases active on p34cdc2 and therefore mimics the phenotype of a point mutation in the site of p34cdc2 phosphorylation. Inhibitors generated in this manner can be used in biochemical and genetic experiments to analyze the catalytic subunits of the kinases that phosphorylate p34cdc2 and represent possible leads for peptidomimetic chemistry to develop drugs that regulate cell proliferation by controlling the activity of p34cdc2.

Pseudosubstrate inhibitors are closely related in sequence to kinase substrates, but lack phosphorylatable residues and function as competitive inhibitors (Hardie, G. (1988). Nature, 592–593). For example, the inhibitor of cyclic AMP-dependent protein kinase is a 75 amino acid peptide that inhibits cyclic AMP-dependent protein kinase with a Ki in vitro of about 1 nM (Ashby, C. D. and Walsh, D. A. (1972). J. Biol. Chem. 247, 6637–6642.). When expressed in vivo, a recombinant derivative of the inhibitor has been demonstrated to affect the transcription of cAMP-responsive genes (Grove, J. R., Price, D. J., Goodman, H. M., and Auruch, J. (1987). Science. 530–533). We have shown that a peptide-*staphylococcal nuclease* chimera that encodes a 22 amino acid sequence derived from this peptide can prevent the proliferation of budding yeast cells in vivo and inhibit the cAMP-dependent protein kinase in vitro.

Several different variables can be investigated using this system. First, different sequences in the nuclease molecule can be tested for their suitability as points at which to introduce the inhibitory peptide. Second, the effect of expressing the inhibitor at different levels can be tested. Because inhibition by pseudosubstrates is competitive, the degree of kinase inactivation should be dose-dependent. Third, libraries in which the inhibitory peptide has been doped to different extents can be tested. This can reveal whether strong kinase inhibitors are rare or common and whether several different sequences are effective. Fourth, the possibility of obtaining temperature-sensitive inhibitors can be evaluated.

To screen for an inhibitor of the kinase active on tyrosine 15 of p34cdc2, we can introduce a library of *staphylococcal nuclease* chimeras containing mutagenized versions of the peptide extending between residues 5 to 25 of p34cdc2 into *Saccharomyces pombe* cells carrying a cdc25ts mutation. At the non permissive temperature cdc25ts cells arrest in G2 as a consequence of high levels of phosphorylation on tyrosine 15 of p34cdc2 (Gould, K. L. and Nurse, P. (1989). Nature 342, 39–45). Cells carrying an effective pseudosubstrate inhibitor of the tyrosine 15 kinase can be identified as those that give rise to viable colonies at 37° C. in a plasmid-linked manner. It is predicted that in these cells, the reduction in the level of tyrosine 15 phosphorylation will allow normal activation of the p34cdc2 kinase. Since the tyrosine phosphorylation of p34cdc2 retards entry into mitosis, expressing inhibitors of tyrosine phosphorylation in wild type cells should accelerate entry into mitosis, causing the cells to divide at a reduced size (Gould, K. L. and Nurse, P. (1989). Nature 342, 39–45). As a control for their specificity, these activities of inhibitors can be checked in cells carrying a cdc2 mutant (F15) that cannot be tyrosine phosphorylated. Inhibitors of the desired type will have no effect in these cells.

An inhibitor thus isolated can be used to identify the tyrosine kinase both in vivo and in vitro. When introduced into weelts cells, p34cdc2 tyrosine kinase inhibitors are expected, like the cdc2-F15 mutant, to cause cell death at the non permissive temperature. This reflects a requirement at different stages of the cell cycle for both phosphorylated and unphosphorylated p34cdc2. If the tyrosine kinase is overexpressed in these cells, increased kinase activity may overcome the effect of the inhibitor and, by phosphorylating p34cdc2, permit cell growth. Thus, it may be possible to isolate the tyrosine kinase form an *Saccharomyces pombe* overexpressing CDNA library as a gene that will suppress the lethality of the combined presence of the kinase inhibitor and absence of weel.

In related experiments, pseudosubstrate inhibitors can be used to investigate the activation of p34cdc2 in animal cells. In budding yeast strains which carry the human cdc2 gene in place the yeast gene, we can generate pseudosubstrate inhibitors of the p34cdc2 kinase itself, and use these inhibitors to probe the G1 and G2 activities of mammalian p34cdc2. Using the shuttle scheme for bacterial expression of inhibitors first identified in eukaryotic cells we can produce large quantities of pseudosubstrate inhibitors that can be used for biochemical experiments. For example, to establish that a kinase identified in fractionated extracts is involved in regulating p34cdc2 in cells, the abilities of several inhibitors to prevent p34cdc2 phosphorylation in vivo and in vitro can be compared. Because pseudosubstrate inhibitors are expected to interact quite strongly with their substrates, they may also be useful as affinity reagents for biochemical purification.

The approach described herein can be extended to the study of any protein phosphorylation in both yeast and animal cells, where genetic selections for alterations in phosphorylation level can be devised (such as induction or reversion of a transformed phenotype). Pseudosubstrate kinase inhibitors can play an important role in drug discovery. By providing structure-function activity correlations they yield important information for the development of small molecule inhibitors by peptidomimetic chemistry or other methods. Knowledge of the biological consequences of a given phosphorylation site makes it possible to select inhibitors of the phosphorylation even when the identity of the kinase that adds the phosphate group is unknown. Three strategies can be used to identify the target of a protein-peptide chimera: 1) selecting those genes whose overexpression abrogates the inhibitory effect of the chimera, 2) identifying protein fusions that interact in a two hybrid assay with a fusion between the peptide-protein chimera and a DNA binding domain, and 3) mass-spectroscopy based identification of proteins that copurify with the protein-peptide chimera. We therefore can use these inhibitors to identify the protein kinases responsible for biological effects thus providing new targets for drug discovery. Pseudosubstrate kinase inhibitors can also have the three applications illustrated above. First, they can permit highly-directed type of genetic suppression analysis. Second, they can serve as a link between genetic and biochemical experiments. Third, they can assist in the analysis of the cell cycle in animal cells.

Protein-peptide chimeras can also be used to select for inhibitors of protein phosphatases, a class of molecules that regulates many different important biological pathways (Hunter 1995 Cell 80:225–236). For example, activity of Cdc25, the phosphatase that removes the phosphate from tyrosine 15 of p34cdc2 essential for viability in a wild-type background, but overexpression of the protein can kill cells that have reduced kinase activity for tyrosine 15 by causing them to enter mitosis prematurely (Russell and Nurse, 1987, Cell 49:559–567). The latter observation makes it possible to select inhibitors that overcome this lethality by inhibiting tyrosine phosphatase activity.

The specific protocol would be to transform a *Schizosaccharomyces pombe* wee1 strain overexpressing Cdc25 with a library of protein-peptide chimeras, and then select cells that could grow at 35° C., the non-permissive temperature for the wee1 mutation. To identify colonies that grew because they contained an inhibitory protein-peptide chimera the entire selection would be repeated. DNA would be extracted from the colonies that grew at 35° C., transformed into bacteria, amplified, retransformed into the starting fission yeast strain, and the selection would be repeated.

The strategy described above can be generalized to identify inhibitors of any protein phosphatase in any cell type into which it is possible to transform and express the DNA elements of a protein-peptide chimera library. As is the case for identification of protein kinase inhibitors such libraries could consist of mutagenized peptides based on a known phosphorylation site or completely random peptide libraries. Using the same approaches described to identify the targets of protein kinases inhibitors it should be possible to isolate the targets of protein phosphatase inhibitors without requiring any prior knowledge of their molecular identity.

The use of the methods described herein as means to manipulate the kinases that phosphorylate p34cdc2 can allow the examination of a number of significant problems including the proteins that couple p34cdc2 activation to the completion of successive events in the cell cycle and how these proteins interact to create effective regulatory circuits. In addition, these methods can facilitate the understanding of the signal through which the doubling of cell mass, the completion of DNA synthesis and the assembly of the mitotic spindle are sensed.

In using these methods, one can focus initially on those proteins that are one step removed in the regulatory hierarchy from the enzymes that directly modify p34cdc2 and then expand to different levels of the regulatory hierarchy as information is gathered. It is likely that these proteins will interact with the kinases and phosphatases whose analysis is described above. The methods can then be utilized in the significant future challenge of determining the molecular nature of the signals generated by incomplete spindles and unreplicated DNA as well as to investigate their generation and reception.

EXAMPLE 5

An experimental plan for the use of this system for the development of inhibitors of protein-protein interactions is herein disclosed. Biochemical pathways characteristically involve the transmission of information via the direct physical interaction proteins. It would be extremely useful if these interactions could be disrupted. An adaptation of the scheme described above can be used for the more general problem of developing chimeric polypeptides that can inhibit the interaction of any two proteins (which will be arbitrary designated X and Y) that have been shown to bind to each other. It is necessary that the region of at least one of the two proteins responsible for their interaction have been identified. Using an approach proposed by Fields and Song (Fields, S. and Song, O. (1989), Nature 340, 245–246), protein X can be linked to the DNA binding domain of the yeast transcriptional regulator GAL4 and protein Y can be linked to a powerful transcriptional activator such as VP16 (McKnight et al., (1987) P.N.A.S. 84, 7061–7065). This can create a situation where the binding of X and Y to each other can be scored genetically in yeast: in cells carrying both of these fusion proteins (but lacking wild-type GAL4), the stimulation of transcription form a GAL1-LacZ reporter construct is dependent upon the ability of X and Y to bring the DNA binding and transcriptional activation domains into physical proximity. In addition, more recent variants of the two hybrid method allow direct selection for inhibition of the interaction between the DNA binding domain and transcriptional activator fusions (Vidal et al, Proceedings of the National Academy of Sciences of the United States of America, Sep. 17, 1996 93(19):10315–20).

In this experimental scheme, the libraries of chimeric peptides could be of three types: i) random fragments of the two interacting proteins, ii) mutagenized derivatives of a particular region of one of the interacting proteins that has previously been identified as being important in the protein-protein interaction, and iii) completely random sequences of short peptides. The chimeras can be expressed in yeast cells and those colonies identified in which expression of the chimera competitively inhibits the binding of proteins X and Y and prevents transcription from the GAL1-LacZ reporter. The success of this scheme is enhanced by the use of the anchored peptides in that it is likely that the surface of the interaction of at least one of the two proteins be determined in large part by a short linear sequence.

Preliminary tests of this scheme can entail interference between the binding of the GAL80 to GAL4. As is known in the art, the GAL80 protein binds to a 30 amino acid stretch of GAL4 that lies between residues 851 and 881 (Ma, J. and Ptashne, M. (1987). Cell 50, 137–142). Ma and Ptashne (Ma, J. and Ptashne, M. (1988). Cell 55, 443–446) have shown that when the transcriptional activator GAL4 is removed and transferred to GAL80, transcription of GAL1-LacZ is dependent upon the interaction of GAL4 and GAL80; LacZ expression therefore serves as a means to assay this association. To create inhibitors, we can introduce sequences 851 to 871 of GAL4, and randomly generated variants, into *staphylococcal nuclease*, and then transform the chimeras into yeast cells and screen for white colonies. The optimization of this approach can be undertaken as described above for pseudosubstrate inhibitors.

The methods in this scheme can in principle be used to study any cellular process that involves protein-protein association (including interactions among the enzymes that regulate p34cdc2). It is likely to be most useful in animal cells, in which conventional molecular genetics is difficult.

In a specific example of the inhibition of protein-protein interaction, these methods can be used to investigate the binding of the product of the retinoblastoma susceptibility locus (the RB protein; Weinberg, R. A. (1990). TIBS 15, 199–202) to E1A and to the SV40 large T antigen. The RB protein forms stable complexes with these proteins and the integrity of the regions of E1A and T antigen involved in RB binding are essential for cellular transformation (e.g. Whyte, P., Buchkovich, K. J., Horowitz, J. M., Friend, S. H., Raybuck, M., Weinberg, R. A. and Harlow, E. (1988). Nature 334, 124–129).

The described methods with this anchored peptide library can allow the development of inhibitors of these interactions. Protein interaction akin to those observed with RB and SV40 T antigen or E1A are particularly attractive for disruption by this technique because very short peptides derived from E1A and SV40 T antigen can associate tightly with RB in a manner analogous to the binding of a receptor to it ligand (Hu, Q., Dyson, N. and Harlow, E. (1990). EMBO J. 9, 1147–1155). Truncated RB proteins (Hu, Q., Dyson, N. and Harlow, E. (1990). EMBO J. 9, 1147–1155) can be linked to the GAL4 DNA binding domain and E1A linked to the transcriptional activator VP16(Sadowski, I., Ma, J., Triezenberg, S. and Ptashne, M. (1988). Nature, 335, 563–564). Regions of E1A implicated in binding to RB can be inserted into nuclease, and libraries of mutagenized chimeras screened for their ability to disrupt the association of E1A and RB. A similar approach can be taken to generate inhibitors of the binding of RB to SV40 large T antigen. We can then express these inhibitors in animal cells and determine if they are able to interfere with the transforming activities of the viral proteins.

As a number of proteins other than RB have been shown to bind to E1A and SV40 T antigen and they are currently being isolated (e.g. Dyson, N., Buchkovich, K. J., Whyte, P. and Harlow, E. (1989). Cell 58, 249–255), it may be possible to reproduce many of these interactions in yeast cells, as described above, and then to screen genetically for inhibitors that will disrupt individual interactions in a highly selective manner. The use of use of the methods described herein in this manner can significantly advance our understanding of the mechanisms that control the proliferation of mammalian cells.

The disclosed methods have several advantages over more conventional microinjection experiments involving peptides or antibodies. Moreover and perhaps most importantly, the use of a genetic screen that can identify rare proteins with high potencies can permit the generation of highly effective and specific inhibitors. In addition, it can be possible to create conditional inhibitors to these interactions by screening the disclosed libraries for chimeras whose activity is temperature sensitive.

EXAMPLE 6

An experimental plan for the use of this system for the analysis of the heat shock response is herein disclosed. The heat shock response is a universal feature of prokaryotic and eukaryotic cells. It involves the homeostatic regulation of heat shock protein (hsp) abundance to maintain a level compatible with growth in both normal and environmentally stressful conditions (Lindquist, S. and Craig, E. A. (1988). Annu. Rev. Genet. 22, 631–677). The disclosed methods can be used to study the mechanisms that are responsible for this homeostasis.

Heat shock proteins act not only to repair thermally damaged proteins following heat shock but also act on newly synthesized proteins in normally growing cells, to facilitate transport across membranes, assembly into multimeric structures and correct folding (Pelham, H. R. B. (1986). Cell 46, 959–961; Bochkavera, E. S., Lissin, N. M., and Girshovich, H. S. (1988). Nature 336, 254–257; Deshaies, R. J., Koch, R. D., Werner-Washbume, M., Craig, E. A. and Schekrnan, R. (1988). Nature 332, 800–805; Hemmingsen, S. M., Woolford, C., van der View, S. M., Tilly, K., Dennis, D. T., Georgopoulos, C. P., Hendrix, R. W., and Ellis, R. J. (1988). Nature 333, 330–334; Gaitanaris, G. A., Papvassilious, A. G., Rubock, P., Silverstein, S. J. and Gottesman, M. E. (1990). Cell 61, 1013–120). Cell viability appears to depend upon maintaining the correct concentration of heat shock proteins: both over-expression (Deshaies, R. J., Koch, R. D., Werner-Washburne, M., Craig, E. A. and Schekman, R. (1988). Nature 332, 800–805) and under-expression (Werner-Washburne, M., Stone, D. and Craig, E. (1987). Mol. Cell. Bio. 7, 2568–2577) are lethal. This suggests that the regulation of heat shock protein synthesis is crucially important to establish the correct intracellular environment for the production of active proteins.

In eucaryotes, control of the rate of heat shock protein synthesis is largely transcriptional and depends upon the activity of heat shock factor (Wu, C. (1985) Nature 317, 84 87).

Genetic selection can be used to identify protein-peptide chimeras that inhibit the transcriptional response to heat shock. To such inhibitors, a gene encoding the potent A fragment of diphtheria toxin (Chen, J. Y. C., Bodley, J. W. and Livingston, D. M. (1985). Mol. Cell. Biol. 5, 3357–3364) can be placed under indirect heat shock factor control. Haploid cells carrying the heat shock factor-responsive toxin can be mutagenized, exposed briefly to heat shock and then plated at low temperature. Among the cells that survive this treatment will be mutants that are defective in the activation of heat shock factor. Extracts from these mutants can then be analyzed for the presence of kinases and phosphatases that modify heat shock factor and, if an in vitro assay has been developed, biochemical complementation can be undertaken.

EXAMPLE 7

Several changes were made to the working construct (designated TT-18) which increased the expression level of the molecular scaffold, *staphylococcal nuclease*, to >5% of all cellular protein. These changes included: installing the strong constitutive PGK1 promoter replacing the single-copy conferring CEN-ARS sequence with the high-copy conferring 2 $\mu$ fragment, and assembling a synthetic *staphy-* lococcal nuclease gene to replace the 47% of rare codons with those most optimal for yeast expression.

A library of peptides resides in an exposed surface loops of a catalytically-inactivated variant of staphylococcal nuclease. Unique EcoR1 and Sal1 restriction sites were engineered into a synthetic staphylococcal nuclease gene so that random oligonucleotide could be inserted in place of those encoding for residues 20–28 of the exposed loop. A current library employs a 77-mer oligonucleotide (Research Genetics) in which the middle 48 bases are specified by NNS, where N is a 1:1:1:1 mixture of T:C:A:G and S is a 2:1 mixture of C:G SEQ ID No:1.

5'-CCC GAA TTC GGT GGT NNS NNS NNS NNS NNS NNS NNS NNS NNS NNS NNS NNS NNS NNS NNS GGT GGT GTC GAC AC-3'

By restricting the third position of every codon, we eliminate 2 of the 3 potential stop codons and bias the library towards preferred codons found in other highly expressed genes. Using this technology, five inhibitors of the pheromone response signal transduction cascade in budding yeast were isolated and identified. Activation of this pathway can be induced by treating yeast cells with alpha factor, a polypeptide that induces cell cycle arrest. Inhibitors of components of this pathway would allow yeast cells to grow in the presence of alpha factor.

In practice, a library of approximately eight million random peptides (displayed from a surface loop of staphylococcal nuclease) was prepared in E. coli. Transformation of a fraction of this plasmid DNA into our selection strain, followed by growth on selective medium (-Ura), resulted in 150,000 yeast transformants. The transformants were collected in culture and spread at a lower cell density onto plates containing 1 ug/mL alpha factor. All of the colonies that grew on the plates (about 400/plate) containing alpha factor were collected, the plasmid DNA was rescued and transformed back into E. coli where it was amplified, isolated and transformed back into our selection strain. Transformants were collected in culture and spread onto plates containing 1 ug/mL alpha factor at the same cell density that was used in the first round of selection. However, instead of obtaining 400 resistant colonies, these plates contained lawns of alpha factor resistant colonies. This was a first indicated that plasmids were rescued and amplified which conferred resistance to alpha factor.

Five clones (designated pTCN27, pTCN34, pTCN43, pTCN44, and pTCN45) were isolated from these plates, sequenced and several experiments were performed. First, we verified that these plasmids confer resistance to alpha factor by showing that alpha factor resistance is lost when the plasmid is lost. Second, we picked two of these clones and showed that the alpha factor resistance is directly related to the random oligonucleotide installed in the loop of staphylococcal nuclease (as opposed to some other portion of the plasmid). This was done by: (1) cutting out the random oligonucleotide from one of the alpha factor resistant plasmids, (2) ligating it into the working construct that had not been through a round of selection, (3) transforming the resulting plasmid into our selection strain, and (4) testing the transformants for resistance to alpha factor. All of the transformants that we tested were resistant to alpha factor.

Figure 14:
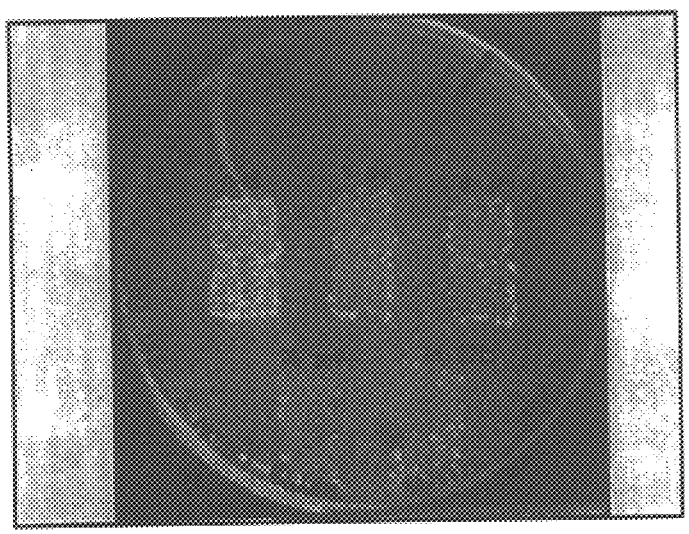
FIG. 14 is a photograph showing yeast expressing staph nuclease having the original loop, wherein the yeast is capable of mating and yeast transformed with a peptide chimera, wherein the yeast is unable to mate.

Alpha-factor induced cell cycle arrest is a necessary step in the mating of budding yeast cells. Therefore, we suspected that our alpha factor resistant plasmids might also confer sterility to cells in a mating assay. Plate 1 of FIG. 14 shows the results of this assay and those patches of cells that are able to mate will form colonies on this plate. The positive control for mating is the working construct (TT-18), which expresses staph nuclease at the same high levels as the resistance conferring plasmids, but the staph nuclease in the positive control does not contain a random peptide in its exposed loop. Negative controls for mating are TA-2094 and -2095. TT-34 and -35 both contain the same alpha factor resistant plasmid and appear to be severely compromised for mating.

Figure 15:
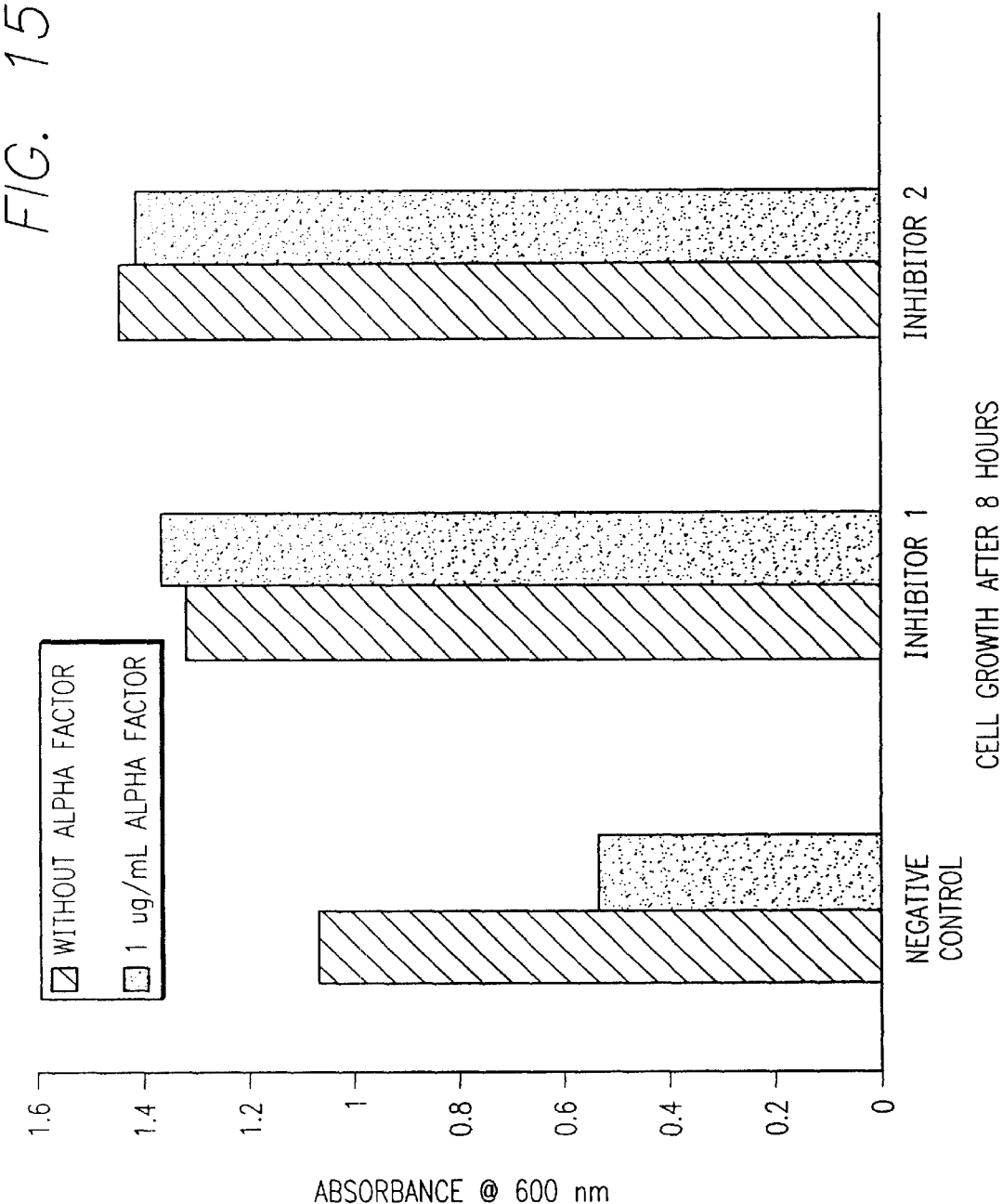
FIG. 15 is a bar graph showing that cells carrying the alpha factor resistant plasmids grow at the same rate in the presence and absence of alpha factor.

Graph 1 of FIG. 15 shows that cells carrying the alpha factor resistant plasmids grow at the same rate in the presence and absence of alpha factor, indicating that the inhibition of cell cycle arrest by the inhibitor peptide in these cells is strong. The negative control for this experiment are cells transformed with our working construct, which expresses staph nuclease at the same high levels as the resistance-conferring plasmids, but the staph nuclease in the negative control does not contain a random peptide in its exposed loop. Cultures of the negative control and inhibitors 1 and 2 were prepared, equalized for absorbance at 600 nm and split into two equal portions (6 samples). Alpha factor (1 ug/mL) was added to one portion of each sample (3 of 6 samples) and all six samples were incubated at 30 degrees centigrade. Cell growth was monitored over an extended time period by measuring the absorbance of each sample at 600 nm. Graph 1 shows data for the eight-hour time point. The negative control, as expected is arrested in the presence of alpha factor, while the growth rate of cells containing inhibitors 1 and 2 appears unaffected by the presence of alpha factor.

Figure 16:
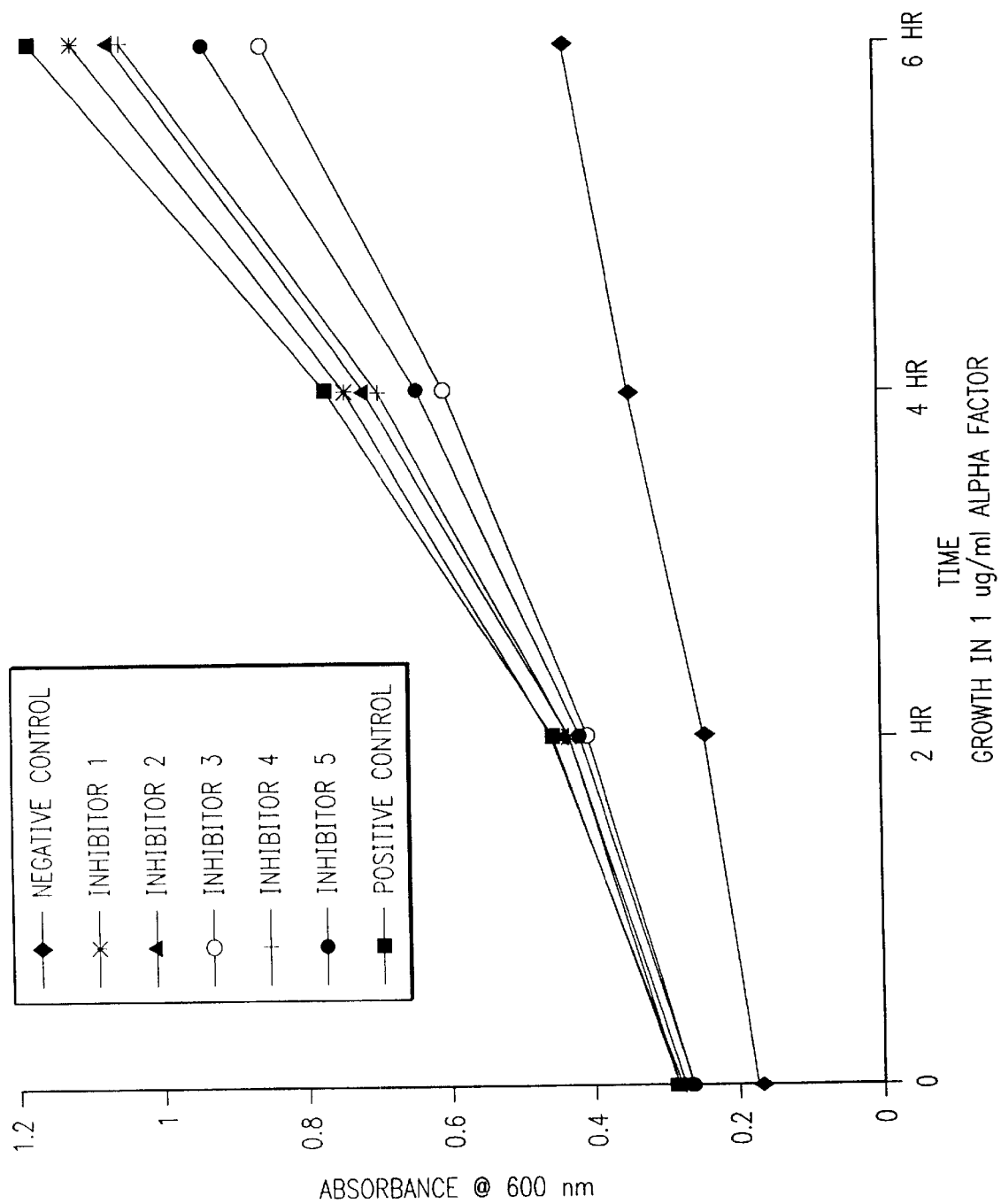
FIG. 16 is a line graph showing that the five inhibitors, i.e., macromolecules, confer comparable resistance to alpha factor as the positive control.

Graph 2 of FIG. 16 shows that the five inhibitors isolated thus far all seem to confer comparable resistance to alpha factor. The negative control in this experiment is the same as that used for Graph 1. The positive control are cells containing a plasmid that confers resistance to alpha factor by expressing a protein involved in silencing of the mating locus. Cultures were prepared and alpha factor (1 ug/mL) was added. Cell growth was monitored over an extended time period by measuring the absorbance of each sample at 600 nm. As expected, growth of the negative control is largely arrested in the presence of alpha factor, while that of the positive control is robust. All five inhibitors grow at rates comparable to the positive control; thus fulfilling the criteria that potent inhibitor peptides produce a phenotype similar to that produced genetically (i.e., the positive control).

What is claimed is:

1. A method for identifying from a library of fusion macromolecules a fusion macromolecule of interest which interacts within a cell with an intracellular target molecule and detecting whether the interaction disrupts a biological pathway, wherein the cell survives or proliferates when the interaction disrupts the biological pathway and the cell dies or fails to proliferate when the interaction does not disrupt the biological pathway, and wherein the macromolecule of interest comprises a peptide library region which is presented in a restricted conformation by a heterologous carrier region, the method comprising:

a) generating a panel of nucleic acid sequences that encodes a peptide library, the panel including a nucleic acid sequence that encodes the peptide library region that interacts with the intracellular target molecule within the cell.

b) inserting the panel of nucleic acid sequences so generated into a plurality of vectors, each vector comprising a carrier region so as to generate an expression library of chimeric vectors. each of the chimeric vectors having a nucleic acid sequence from the panel and a nucleic acid sequence encoding the carrier region having the restricted conformation;

c) introducing the expression library of chimeric vectors into a plurality of cells that lack a recombinant reporter gene so as to generate a library of cells;

d) growing the library of cells so generated under suitable conditions so as to produce a library of fusion macromolecules within the cells, wherein the library of fusion macromolecules comprises the peptide library region presented in a restricted conformation by the carrier region; and e) selecting from the library of cells so grown a desired cell that produces the macromolecule of interest by detecting the interaction between the peptide library region and the target molecule which results in disruption of the biological pathway within the desired cell and enables the desired cell to survive or proliferate, thereby identifying the macromolecule produced by the cell so selected.

2. The method of claim 1, wherein the interaction in step e) between the peptide library region and the target molecule inhibits the target molecule thereby disrupting the biological pathway within the desired cell.

3. The method of claim 1, wherein the biological pathway is a phosphorylation pathway mediated by a cAMP-dependent kinase.

4. The method of claim 1, wherein the biological pathway is a yeast pheromone response pathway.

5. The method of claim 1, wherein the biological pathway is a cell cycle arrest pathway.

6. The method of claim 1, wherein the biological pathway is a cell DNA damage checkpoint pathway.

7. The method of claim 1, wherein the biological pathway is a cellular spindle assembly checkpoint pathway.

8. The method of claim 1, wherein the biological pathway is a heat shock pathway.

9. The method of claim 1, wherein each of the plurality of vactors of step b) further comprises at least one promoter.

10. The method of claim 9, wherein the promoter is selected from a group consisting of a bacterial promoter and a yeast promoter.

11. The method of claim 9, wherein the promoter is an inducible promoter.

12. The method of claim 11, wherein the inducible promoter is selected from a group consisiting of GAL 1, HSP, CUP 1, PGK 1 and PhoA.

13. The method of claim 9, wherein the promoter is a constitutive promoter.

14. The method of claim 13, wherein the constitutive promoter is selected from a group consisting of VP16 and ADH 1.

15. The method of claim 1, wherein the carrier region of the macromolecule comprises the nuclease loop of *Staphyloccus aureus*.

16. The method of claim 1, wherein the biological pathway and the intracellular target molecule yeast pheromone pathway and the target molecule is a G-protein coupled receptor, or the biological pathway is a cell cycle arrest pathway and the target molecule is a p34 molecule, or the biological pathway is a cellular DNA damage check point pathway and the target molecule is a cdc5-ad molecule, or the biological pathway is a cellular spindle assembly checkpoint pathway and the target molecule is an Mps1 molecule.

* * * * *

SEQUENCE LISTING

<160> NUMBER OF SEQ ID NOS: 18

<210> SEQ ID NO 1
<211> LENGTH: 77
<212> TYPE: DNA
<213> ORGANISM: synthetic Staphylococcus aureus nuclease gene

```
<220> FEATURE:
<221> NAME/KEY: misc_feature
<222> LOCATION: (16)..(17)
<223> OTHER INFORMATION: any nucleotide (i.e. a, c, g or t)
<220> FEATURE:
<221> NAME/KEY: misc_feature
<222> LOCATION: (18)
<223> OTHER INFORMATION: g or c
<220> FEATURE:
<221> NAME/KEY: misc_feature
<222> LOCATION: (19)..(20)
<223> OTHER INFORMATION: any nucleotide (i.e. a, c, g or t)
<220> FEATURE:
<221> NAME/KEY: misc_feature
<222> LOCATION: (21)
<223> OTHER INFORMATION: g or c
<220> FEATURE:
<221> NAME/KEY: misc_feature
<222> LOCATION: (22)..(23)
<223> OTHER INFORMATION: any nucleotide (i.e. a, c, g or t)
<220> FEATURE:
<221> NAME/KEY: misc_feature
<222> LOCATION: (24)
<223> OTHER INFORMATION: g or c
<220> FEATURE:
<221> NAME/KEY: misc_feature
<222> LOCATION: (25)..(26)
<223> OTHER INFORMATION: any nucleotide (i.e. a, c, g or t)
<220> FEATURE:
<221> NAME/KEY: misc_feature
<222> LOCATION: (27)
<223> OTHER INFORMATION: g or c
<220> FEATURE:
<221> NAME/KEY: misc_feature
<222> LOCATION: (28)..(29)
<223> OTHER INFORMATION: any nucleotide (i.e. a, c, g or t)
<220> FEATURE:
<221> NAME/KEY: misc_feature
<222> LOCATION: (30)
<223> OTHER INFORMATION: g or c
<220> FEATURE:
<221> NAME/KEY: misc_feature
<222> LOCATION: (31)..(32)
<223> OTHER INFORMATION: any nucleotide (i.e. a, c, g or t)
<220> FEATURE:
<221> NAME/KEY: misc_feature
<222> LOCATION: (33)
<223> OTHER INFORMATION: g or c
<220> FEATURE:
<221> NAME/KEY: misc_feature
<222> LOCATION: (34)..(35)
<223> OTHER INFORMATION: any nucleotide (i.e. a, c, g or t)
<220> FEATURE:
<221> NAME/KEY: misc_feature
<222> LOCATION: (36)
<223> OTHER INFORMATION: g or c
<220> FEATURE:
<221> NAME/KEY: misc_feature
<222> LOCATION: (37)..(38)
<223> OTHER INFORMATION: any nucleotide (i.e. a, c, g or t)
<220> FEATURE:
<221> NAME/KEY: misc_feature
<222> LOCATION: (39)
<223> OTHER INFORMATION: g or c
<220> FEATURE:
<221> NAME/KEY: misc_feature
<222> LOCATION: (40)..(41)
<223> OTHER INFORMATION: any nucleotide (i.e. a, c, g or t)
<220> FEATURE:
<221> NAME/KEY: misc_feature
<222> LOCATION: (42)
<223> OTHER INFORMATION: g or c
<220> FEATURE:
<221> NAME/KEY: misc_feature
<222> LOCATION: (43)..(44)
<223> OTHER INFORMATION: any nucleotide (i.e. a, c, g or t)
<220> FEATURE:
<221> NAME/KEY: misc_feature
<222> LOCATION: (45)
```

```
<223> OTHER INFORMATION: g or c
<220> FEATURE:
<221> NAME/KEY: misc_feature
<222> LOCATION: (46)..(47)
<223> OTHER INFORMATION: any nucleotide (i.e. a, c, g or t)
<220> FEATURE:
<221> NAME/KEY: misc_feature
<222> LOCATION: (48)
<223> OTHER INFORMATION: g or c
<220> FEATURE:
<221> NAME/KEY: misc_feature
<222> LOCATION: (49)..(50)
<223> OTHER INFORMATION: any nucleotide (i.e. a, c, g or t)
<220> FEATURE:
<221> NAME/KEY: misc_feature
<222> LOCATION: (51)
<223> OTHER INFORMATION: g or c
<220> FEATURE:
<221> NAME/KEY: misc_feature
<222> LOCATION: (52)..(53)
<223> OTHER INFORMATION: any nucleotide (i.e. a, c, g or t)
<220> FEATURE:
<221> NAME/KEY: misc_feature
<222> LOCATION: (54)
<223> OTHER INFORMATION: g or c
<220> FEATURE:
<221> NAME/KEY: misc_feature
<222> LOCATION: (55)..(56)
<223> OTHER INFORMATION: any nucleotide (i.e. a, c, g or t)
<220> FEATURE:
<221> NAME/KEY: misc_feature
<222> LOCATION: (57)
<223> OTHER INFORMATION: g or c
<220> FEATURE:
<221> NAME/KEY: misc_feature
<222> LOCATION: (58)..(59)
<223> OTHER INFORMATION: any nucleotide (i.e. a, c, g or t)
<220> FEATURE:
<221> NAME/KEY: misc_feature
<222> LOCATION: (60)
<223> OTHER INFORMATION: g or c
<220> FEATURE:
<221> NAME/KEY: misc_feature
<222> LOCATION: (61)..(62)
<223> OTHER INFORMATION: any nucleotide (i.e. a, c, g or t)
<220> FEATURE:
<221> NAME/KEY: misc_feature
<222> LOCATION: (63)
<223> OTHER INFORMATION: g or c

<400> SEQUENCE: 1
cccgaattcg gtggtnnsnn snnsnnsnns nnsnnsnnsn nsnnsnnsnn snnsnnsnns      60
nnsggtggtg tcgacac                                                    77

<210> SEQ ID NO 2
<211> LENGTH: 231
<212> TYPE: PRT
<213> ORGANISM: amino acid sequence of Staphylococcus aureus native
      nuclease

<400> SEQUENCE: 2

Met Leu Val Met Thr Glu Tyr Leu Leu Ser Ala Gly Ile Cys Met Ala
 1               5                  10                  15

Ile Val Ser Ile Leu Leu Ile Gly Met Ala Ile Ser Asn Val Ser Lys
                20                  25                  30

Gly Gln Tyr Ala Lys Arg Phe Phe Phe Phe Ala Thr Ser Cys Leu Val
            35                  40                  45

Leu Thr Leu Val Val Val Ser Ser Leu Ser Ser Ser Ala Asn Ala Ser
        50                  55                  60

Gln Thr Asp Asn Gly Val Asn Arg Ser Gly Ser Glu Asp Pro Thr Val
65                  70                  75                  80
```

```
Tyr Ser Ala Thr Ser Thr Lys Lys Leu His Lys Glu Pro Ala Thr Leu
                85                  90                  95

Ile Lys Ala Ile Asp Gly Asp Thr Val Lys Leu Met Tyr Lys Gly Gln
            100                 105                 110

Pro Met Thr Phe Arg Leu Leu Leu Val Asp Thr Pro Glu Thr Lys His
            115                 120                 125

Pro Lys Lys Gly Val Glu Lys Tyr Gly Pro Glu Ala Ser Ala Phe Thr
        130                 135                 140

Lys Lys Met Val Glu Asn Ala Lys Lys Ile Glu Val Glu Phe Asp Lys
145                 150                 155                 160

Gly Gln Arg Thr Asp Lys Tyr Gly Arg Gly Leu Ala Tyr Ile Tyr Ala
                165                 170                 175

Asp Gly Lys Met Val Asn Glu Ala Leu Val Arg Gln Gly Leu Ala Lys
            180                 185                 190

Val Ala Tyr Val Tyr Lys Pro Asn Asn Thr His Glu Gln His Leu Arg
        195                 200                 205

Lys Ser Glu Ala Gln Ala Lys Lys Glu Lys Leu Asn Ile Trp Ser Glu
    210                 215                 220

Asp Asn Ala Asp Ser Gly Gln
225                 230

<210> SEQ ID NO 3
<211> LENGTH: 150
<212> TYPE: PRT
<213> ORGANISM: amino acid sequence of Staphylococcus aureus native
      nuclease

<400> SEQUENCE: 3

Ser Ala Thr Ser Thr Lys Lys Leu His Lys Glu Pro Ala Thr Leu Ile
1               5                   10                  15

Lys Ala Ile Asp Gly Asp Thr Val Lys Leu Met Tyr Lys Gly Gln Pro
            20                  25                  30

Met Thr Phe Arg Leu Leu Leu Val Asp Thr Pro Glu Thr Lys His Pro
        35                  40                  45

Lys Lys Gly Val Glu Lys Tyr Gly Pro Glu Ala Ser Ala Phe Thr Lys
    50                  55                  60

Lys Met Val Glu Asn Ala Lys Lys Ile Glu Val Glu Phe Asp Lys Gly
65                  70                  75                  80

Gln Arg Thr Asp Lys Tyr Gly Arg Gly Leu Ala Tyr Ile Tyr Ala Asp
                85                  90                  95

Gly Lys Met Val Asn Glu Ala Leu Val Arg Gln Gly Leu Ala Lys Val
            100                 105                 110

Ala Tyr Val Tyr Lys Pro Asn Asn Thr His Glu Gln His Leu Arg Lys
        115                 120                 125

Ser Glu Ala Gln Ala Lys Lys Glu Lys Leu Asn Ile Trp Ser Glu Asp
    130                 135                 140

Asn Ala Asp Ser Gly Gln
145                 150

<210> SEQ ID NO 4
<211> LENGTH: 177
<212> TYPE: PRT
<213> ORGANISM: amino acid sequence of Staphylococcus aureus nuclease
      protein

<400> SEQUENCE: 4
```

```
Met Tyr Pro Tyr Asp Val Pro Asp Tyr Ala Ser Leu Pro Gly Ile Gln
 1               5                  10                  15

Pro Ala Thr Ser Thr Lys Lys Leu His Lys Glu Pro Ala Thr Leu Ile
                20                  25                  30

Lys Ala Ile Asp Gly Thr Thr Val Lys Leu Met Tyr Lys Gly Gln Pro
                35                  40                  45

Met Thr Phe Arg Leu Leu Leu Val Asp Thr Pro Glu Phe Lys Ala Lys
         50                  55                  60

Ser Pro Lys Lys Ala Leu Glu Lys Tyr Gly Pro Glu Ala Ser Ala Phe
 65                  70                  75                  80

Thr Lys Lys Met Val Glu Asn Ala Lys Lys Ile Glu Val Glu Phe Asp
                 85                  90                  95

Lys Gly Gln Arg Thr Asp Lys Tyr Gly Arg Gly Leu Ala Tyr Ile Tyr
                100                 105                 110

Ala Asp Gly Lys Met Val Asn Glu Ala Leu Val Arg Gln Gly Leu Ala
                115                 120                 125

Lys Val Ala Tyr Val Tyr Lys Pro Asn Asn Thr His Glu Gln His Leu
                130                 135                 140

Arg Lys Ser Glu Ala Gln Ala Lys Lys Glu Lys Leu Asn Ile Trp Ser
145                 150                 155                 160

Glu Asp Asn Ala Asp Ser Gly Gln Val Asp Val His His His His His
                165                 170                 175

His
```

```
<210> SEQ ID NO 5
<211> LENGTH: 12
<212> TYPE: PRT
<213> ORGANISM: amino acid sequence of Staphylococcus aureus nuclease
      protein

<400> SEQUENCE: 5

Tyr Pro Tyr Asp Val Pro Asp Tyr Ala Ser Leu Pro
 1               5                  10

<210> SEQ ID NO 6
<211> LENGTH: 12
<212> TYPE: PRT
<213> ORGANISM: amino acid sequence of Staphylococcus aureus nuclease
      protein

<400> SEQUENCE: 6

Thr Pro Glu Phe Lys Ala Lys Ser Pro Lys Lys Ala
 1               5                  10

<210> SEQ ID NO 7
<211> LENGTH: 6
<212> TYPE: PRT
<213> ORGANISM: amino acid sequence of Staphylococcus aureus nuclease
      protein

<400> SEQUENCE: 7

His His His His His His
 1               5

<210> SEQ ID NO 8
<211> LENGTH: 7358
<212> TYPE: DNA
<213> ORGANISM: nucleic acid sequence of plasmid PSF248

<400> SEQUENCE: 8
```

-continued

```
gaattaattc caccgcggtg gcggccaatt ctcatgtttg acagcttatc atcgatggat      60
aagcatgaat atcggcttcg cggtcacagc acgcatcacg ttgctcatca tgctgcccat     120
gcgtaaccgg ctagttgcgg ccgctgccag ccatttgcca ctctccttt catccgcatc      180 ggcagggtca tccgggcgca tccaccactc ctgatgcagt aatcctacgg tgcggaatgt     240
ggtggcctcg aaattctgtc ataaagttgt cacggccgag acttatagtc gctttgtttt     300
tattttttaa tgtatttgta catggagaaa ataaagtgaa acaaacgact attgcactgg     360
cactcttacc gttactgttt accctgtga caaaagcccg gatccccaat tcactggccg       420
tcgttttaca acgtcgtgac tgggaaaacc ctggcgttac ccaacttaat cgccttgcag     480
cacatccccc tttcgccagc tggcgtaata gcgaagaggc ccgcaccgat cgcccttccc     540
aacagttgcg cagcctgaat ggcgaatggc gcctgatgcg gtattttctc cttacgcatc     600
tgtgcggtat ttcacaccgc atatatcgct gggccattct catgaagaat atcttgaatt     660
tattgtcata ttactagttg gtgtggaagt ccatatatcg gtgatcaata tagtggttga     720
catgctggct agtcaacatt gagccttttg atcatgcaaa tatattacgg tattttacaa     780
tcaaatatca aacttaacta ttgactttat aacttattta ggtggtaaca ttcttataaa     840
aaagaaaaaa attactgcaa aacagtacta gcttttaact tgtatcctag gttatctatg     900
ctgtctcacc atagagaata ttacctattt cagaatgtat gtccatgatt cgccgggtaa     960
atacatataa tacacaaatc tggcttaata aagtctataa tatatctcat aaagaagtgc    1020
taaattggct agtgctatat attttttaaga aaatttcttt tgactaagtc catatcgact   1080
ttgtaaaagt tcactttagc atacatatat tacgagcc agaaattgta acttttgcct      1140
aaaatcacaa attgcaaaat ttaattgctt gcaaaaggtc acatgcttat aatcaacttt    1200
tttaaaaatt taaaatactt tttattttt tattttaaa cataaatgaa ataatttatt      1260
tattgtttat gattaccgaa acataaaacc tgctcaagaa aaagaaactg ttttgtcctt    1320
ggaaaaaaag cactacctag gagcggccaa aatgccgagg ctttcatagc ttaaactctt    1380
tacagaaaat aggcattata gatcagttcg agttttctta ttcttccttc cggttttatc    1440
gtcacagttt tacagtaaat aagtatcacc tcttagagtt cgatgataag ctgtcaaaca    1500
tgagaattaa ttccacatgt taaaatagta aaggagcatg ttcggcacac agtggaccga    1560
acgtggggta agtgcactag ggtccggtta aacggatctc gcattgatga ggcaacgcta    1620
attatcaaca tatagattgt tatctatctg catgaacacg aaatctttac ttgacgactt    1680
gaggctgatg gtgtttatgc aaagaaacca ctgtgtttaa tatgtgtcac tgtttgatat    1740
tactgtcagc gtagaagata atagtaaaag cggttaataa gtgtatttga ataagtgtg     1800 ataaagtttt tacagcgaaa agacgataaa tacaagaaaa tgattacgag gatacggaga    1860
gaggtatgta catgtgtatt tatatactaa gctgccggcg gttgtttgca agaccgagaa    1920
aaggctagca agaatcgggt cattgtagcg tatgcgcctg tgaacattct cttcaacaag    1980
tttgattcca ttgcggtgaa atggtaaaag tcaaccccct gcgatgtata ttttcctgta    2040
caatcaatca aaaagccaaa tgatttagca ttatctttac atcttgttat tttacagatt    2100
ttatgtttag atctttatg cttgcttttc aaaaggcttg caggcaagtg cacaaacaat     2160
acttaaataa atactactca gtaataacct atttcttagc attttttgacg aaatttgcta   2220 ttttgttaga gtcttttaca ccatttgtct ccacacctcc gcttacatca acaccaataa    2280
cgccatttaa tctaagcgca tcaccaacat tttctggcgt cagtccacca gctaacataa    2340
aatgtaagct ctcggggctc tcttgccttc caacccagtc agaaatcgag ttccaatcca    2400
```

-continued

```
aaagttcacc tgtcccacct gcttctgaat caaacaaggg aataaacgaa tgaggtttct    2460
gtgaagctgc actgagtagt atgttgcagt cttttggaaa tacgagtctt ttaataactg    2520
gcaaaccgag gaactcttgg tattcttgcc acgactcatc tccatgcagt tggacgatcg    2580
atgataagct gtcaaacatg agaattgggt aataactgat ataattaaat tgaagctcta    2640
atttgtgagt ttagtataca tgcatttact tataatacag ttttttagtt ttgctggccg    2700
catcttctca aatatgcttc ccagcctgct tttctgtaac gttcaccctc taccttagca    2760
tcccttccct ttgcaaatag tcctcttcca acaataataa tgtcagatcc tgtagagacc    2820
acatcatcca cggttctata ctgttgaccc aatgcgtctc ccttgtcatc taaacccaca    2880
ccgggtgtca taatcaacca atcgtaacct tcatctcttc cacccatgtc tctttgagca    2940
ataaagccga taacaaaatc tttgtcgctc ttcgcaatgt caacagtacc cttagtatat    3000
tctccagtag atagggagcc cttgcatgac aattctgcta acatcaaaag gcctctaggt    3060
tcctttgtta cttcttctgc cgcctgcttc aaaccgctaa caatacctgg gcccaccaca    3120
ccgtgtgcat tcgtaatgtc tgcccattct gctattctgt atacccccgc agagtactgc    3180
aatttgactg tattaccaat gtcagcaaat tttctgtctt cgaagagtaa aaaattgtac    3240
ttggcggata atgcctttag cggcttaact gtgccctcca tggaaaaatc agtcaagata    3300
tccacatgtg ttttttagtaa acaaattttg ggacctaatg cttcaactaa ctccagtaat    3360
tccttggtgg tacgaacatc caatgaagca cacaagtttg tttgctttc gtgcatgata    3420 ttaaatagct tggcagcaac aggactagga tgagtagcag cacgttcctt atatgtagct    3480
ttcgacatga tttatcttcg tttcctgcag gttttttgttc tgtgcagttg ggttaagaat    3540
actgggcaat ttcatgtttc ttcaacacca catatgcgta tatataccaa tctaagtctg    3600
tgctccttcc ttcgttcttc cttctgctcg gagattaccg aatcaaaaaa atttcaaaga    3660
aaccggaatc aaaaaaaaga acaaaaaaaa aaaagatgaa ttgaaaagct tatcgatacc    3720
gtcgactgct cattgctata ttgaagtacg gattagaagc cgccgagcgg gtgacagccc    3780
tccgaaggaa gactctcctc cgtgcgtcct cgtcttcacc ggtcgcgttc ctgaaacgca    3840
gatgtgcctc gcgccgcact gctccgaaca ataaagattc tacaatacta gctttatgg    3900 ttatgaagag gaaaaattgg cagtaacctg gccccacaaa ccttcaaatg aacgaatcaa    3960
attaacaacc ataggatgat aatgcgatta gttttttagc cttattctg gggtaattaa    4020 tcagcgaagc gatgattttt gatctattaa cagatatata aatgcaaaaa ctgcataacc    4080
actttaacta atactttcaa cattttcggt ttgtattact tcttattcaa atgtaataaa    4140
agtatcaaca aaaattgtt aatatacctc tatactttaa cgtcaggag aaaaaatatt    4200 aatgtaccca tatgatgttc cagattacgc ttctttgccc gggatccagc cggcaacttc    4260
aactaaaaaa ttacataaag aacctgcgac tttaattaaa gcgattgatg gtaccacggt    4320
taaattaatg tacaaaggtc aaccaatgac attcagacta ttattggttg atacacctga    4380
attcaaggct aagtctccaa agaaggctct cgagaaatat ggtcctgaag caagtgcatt    4440
tacgaaaaaa atggtagaaa atgcaaagaa aattgaagtc gagtttgaca aaggtcaaag    4500
aactgataaa tatggacgtg gcttagcgta tatttatgct gatggaaaaa tggtaaacga    4560
agctttagtt cgtcaaggct tggctaaagt tgcttatgtt acaaaaccta acaatacaca    4620
tgaacaacat ttaagaaaaa gtgaagcaca agcgaaaaaa gagaaattaa atatttggag    4680
cgaagacaac gctgattcag gtcaagtcga cgtccatcac catcaccatc actaatgctc    4740
```

-continued

```
attgtaaaag tgtcactgct gctagtggca cttttatat ttttagatcc tctacgccgg    4800
acgcatcgtg gccggcatca ccggcgccac aggtgcggtt gctggcgcct atatcgccga    4860
catcaccgat ggggaagatc gggctcgcca cttcgggctc atgagcgctt gtttcggcgt    4920
gggtatggtg gcaggccccg tggccggggg actgttgggc gccatctcct tgcatgcacc    4980
attccttgcg gcgcggtgc tcaacggcct caacctacta ctgggctgct tcctaatgca    5040
ggagtcgcat aagggagagc gtcgacctgc ctcgcgcgtt tcggtgatga cggtgaaaac    5100
ctctgacaca tgcagctccc ggagacggtc acagcttgtc tgtaagcgga tgccgggagc    5160
agacaagccc gtcagggcgc gtcagcgggt gttggcgggt gtcggggcgc agccatgacc    5220
cagtcacgta gcgatagcgg agtgtatact ggcttaacta tgcggcatca gagcagattg    5280
tactgagagt gcaccatatg cggtgtgaaa taccgcacag atgcgtaagg agaaaatacc    5340
gcatcaggcg ctcttccgct tcctcgctca ctgactcgct gcgctcggtc gttcggctgc    5400
ggcgagcggt atcagctcac tcaaaggcgg taatacggtt atccacagaa tcaggggata    5460
acgcaggaaa gaacatgtga gcaaaaggcc agcaaaaggc caggaaccgt aaaaaggccg    5520
cgttgctggc gtttttccat aggctccgcc ccctgacga gcatcacaaa aatcgacgct    5580
caagtcagag gtggcgaaac ccgacaggac tataaagata ccaggcgttt ccccctggaa    5640
gctccctcgt gcgctctcct gttccgaccc tgccgcttac cggatacctg tccgcctttc    5700
tcccttcggg aagcgtggcg ctttctcata gctcacgctg taggtatctc agttcggtgt    5760
aggtcgttcg ctccaagctg gctgtgtgc acgaaccccc cgttcagccc gaccgctgcg    5820
ccttatccgg taactatcgt cttgagtcca acccggtaag acacgactta tcgccactgg    5880
cagcagccac tggtaacagg attagcagag cgaggtatgt aggcggtgct acagagttct    5940
tgaagtggtg gcctaactac ggctacacta aggacagt atttggtatc tgcgctctgc    6000
tgaagccagt taccttcgga aaagagttg gtagctcttg atccggcaaa caaccaccg    6060 ctggtagcgg tggttttttt gtttgcaagc agcagattac gcgcagaaaa aaggatctc    6120 aagaagatcc tttgatcttt tctacggggt ctgacgctca gtggaacgaa aactcacgtt    6180
aagggatttt ggtcatgaga ttatcaaaaa ggatcttcac ctagatcctt ttaaattaaa    6240
aatgaagttt taaatcaatc taagtatat atgagtaaac ttggtctgac agttaccaat    6300
gcttaatcag tgaggcacct atctcagcga tctgtctatt tcgttcatcc atagttgcct    6360
gactccccgt cgtgtagata actacgatac gggagggctt accatctggc cccagtgctg    6420
caatgatacc gcgagaccca cgctcaccgg ctccagattt atcagcaata aaccagccag    6480
ccggaagggc cgagcgcaga agtggtcctg caactttatc cgcctccatc cagtctatta    6540
attgttgccg ggaagctaga gtaagtagtt cgccagttaa tagtttgcgc aacgttgttg    6600
ccattgctgc aggcatcgtg gtgtcacgct cgtcgtttgg tatggcttca ttcagctccg    6660
gttcccaacg atcaaggcga gttacatgat cccccatgtt gtgcaaaaa gcggttagct    6720 ccttcggtcc tccgatcgtt gtcagaagta agttggccgc agtgttatca ctcatggtta    6780
tggcagcact gcataattct cttactgtca tgccatccgt aagatgcttt tctgtgactg    6840
gtgagtactc aaccaagtca ttctgagaat agtgtatgcg gcgaccgagt tgctcttgcc    6900
cggcgtcaac acgggataat accgcgccac atagcagaac tttaaaagtg ctcatcattg    6960
gaaaacgttc ttcggggcga aaactctcaa ggatcttacc gctgttgaga tccagttcga    7020
tgtaacccac tcgtgcaccc aactgatctt cagcatcttt tactttcacc agcgtttctg    7080
ggtgagcaaa aacaggaagg caaaatgccg caaaaaaggg aataagggcg acacggaaat    7140
```

```
gttgaatact catactcttc cttttcaat attattgaag catttatcag ggttattgtc    7200
tcatgagcgg atacatattt gaatgtattt agaaaaataa acaaataggg gttccgcgca    7260
catttccccg aaaagtgcca cctgacgtct aagaaaccat tattatcatg acattaacct    7320
ataaaaatag gcgtatcacg aggccctttc gtcttcaa                           7358

<210> SEQ ID NO 9
<211> LENGTH: 3516
<212> TYPE: DNA
<213> ORGANISM: nucleic acid sequence of PSF248 plasmid

<400> SEQUENCE: 9
gaattaattc caccgcggtg gcggccaatt ctcatgtttg acagcttatc atcgatggat     60
aagcatgaat atcggcttcg cggtcacagc acgcatcacg ttgctcatca tgctgcccat    120
gcgtaaccgg ctagttgcgg ccgctgccag ccatttgcca ctctcctttt catccgcatc    180
ggcagggtca tccgggcgca tccaccactc ctgatgcagt aatcctacgg tgcggaatgt    240
ggtggcctcg aaattctgtc ataaagttgt cacggccgag acttatagtc gctttgtttt    300 tatttttaa tgtatttgta catggagaaa ataaagtgaa acaaacgact attgcactgg    360
cactcttacc gttactgttt accctgtga caaaagcccg gatccagccg gcaacttcaa    420
ctaaaaaatt acataaagaa cctgcgactt taattaaagc gattgatggt accacggtta    480
aattaatgta caaggtcaa ccaatgacat tcagactatt attggttgat acacctgaat    540
tcaaggctaa gtctccaaag aaggctctcg agaaatatgg tcctgaagca agtgcattta    600 cgaaaaaat ggtagaaaat gcaaagaaaa ttgaagtcga gtttgacaaa ggtcaaagaa    660
ctgataaata tggacgtggc ttagcgtata tttatgctga tggaaaaatg gtaaacgaag    720
ctttagttcg tcaaggcttg gctaaagttg cttatgttta caaacctaac aatacacatg    780
aacaacattt aagaaaaagt gaagcacaag cgaaaaaaga gaaattaaat atttggagcg    840
aagacaacgc tgattcaggt caagtcgacg tccatcacca tcaccatcac taatgctcat    900
tgtaaaagtg tcactgctgc tagtggcact tttataattt ttagatcctc tacgccggac    960
gcatcgtggc cggcatcacc ggcgccacag gtgcggttgc tggcgcctat atcgccgaca   1020
tcaccgatgg ggaagatcgg gctcgccact tcgggctcat gagcgcttgt ttcggcgtgg   1080
gtatggtggc aggccccgtg gccggggac tgttgggcgc catctccttg catgcaccat   1140
tccttgcggc ggcggtgctc aacggcctca acctactact gggctgcttc ctaatgcagg   1200
agtcgcataa gggagagcgt cgacctgcct cgcgcgtttc ggtgatgacg gtgaaaacct   1260
ctgacacatg cagctcccgg agacggtcac agcttgtctg taagcggatg ccgggagcag   1320
acaagcccgt cagggcgcgt cagcgggtgt tggcgggtgt cggggcgcag ccatgaccca   1380
gtcacgtagc gatagcggag tgtatactgg cttaactatg cggcatcaga gcagattgta   1440
ctgagagtgc accatatgcg gtgtgaaata ccgcacagat gcgtaaggag aaaataccgc   1500
atcaggcgct cttccgcttc ctcgctcact gactcgctgc gctcggtcgt tcggctgcgg   1560
cgagcggtat cagctcactc aaaggcggta atacggttat ccacagaatc aggggataac   1620
gcaggaaaga acatgtgagc aaaaggccag caaaaggcca ggaaccgtaa aaaggccgcg   1680
ttgctggcgt ttttccatag gctccgcccc cctgacgagc atcacaaaaa tcgacgctca   1740
agtcagaggt ggcgaaaccc gacaggacta taaagatacc aggcgtttcc ccctggaagc   1800
tccctcgtgc gctctcctgt tccgaccctg ccgcttaccg gatacctgtc gcctttctc    1860
```

-continued

```
ccttcgggaa gcgtggcgct ttctcatagc tcacgctgta ggtatctcag ttcggtgtag    1920
gtcgttcgct ccaagctggg ctgtgtgcac gaaccccccg ttcagcccga ccgctgcgcc    1980
ttatccggta actatcgtct tgagtccaac ccggtaagac acgacttatc gccactggca    2040
gcagccactg gtaacaggat tagcagagcg aggtatgtag gcggtgctac agagttcttg    2100
aagtggtggc ctaactacgg ctacactaga aggacagtat ttggtatctg cgctctgctg    2160
aagccagtta ccttcggaaa aagagttggt agctcttgat ccggcaaaca aaccaccgct    2220
ggtagcggtg gtttttttgt ttgcaagcag cagattacgc gcagaaaaaa aggatctcaa    2280
gaagatcctt tgatcttttc tacggggtct gacgctcagt ggaacgaaaa ctcacgttaa    2340
gggattttgg tcatgagatt atcaaaaagg atcttcacct agatcctttt aaattaaaaa    2400
tgaagtttta aatcaatcta agtatatat gagtaaactt ggtctgacag ttaccaatgc    2460
ttaatcagtg aggcacctat ctcagcgatc tgtctatttc gttcatccat agttgcctga    2520
ctccccgtcg tgtagataac tacgatacgg gagggcttac catctggccc cagtgctgca    2580
atgataccgc gagacccacg ctcaccggct ccagatttat cagcaataaa ccagccagcc    2640
ggaagggccg agcgcagaag tggtcctgca actttatccg cctccatcca gtctattaat    2700
tgttgccggg aagctagagt aagtagttcg ccagttaata gtttgcgcaa cgttgttgcc    2760
attgctgcag gcatcgtggt gtcacgctcg tcgtttggta tggcttcatt cagctccggt    2820
tcccaacgat caaggcgagt tacatgatcc cccatgttgt gcaaaaaagc ggttagctcc    2880
ttcggtcctc cgatcgttgt cagaagtaag ttggccgcag tgttatcact catggttatg    2940
gcagcactgc ataattctct tactgtcatg ccatccgtaa gatgcttttc tgtgactggt    3000
gagtactcaa ccaagtcatt ctgagaatag tgtatgcggc gaccgagttg ctcttgcccg    3060
gcgtcaacac gggataatac cgcgccacat agcagaactt taaaagtgct catcattgga    3120
aaacgttctt cggggcgaaa actctcaagg atcttaccgc tgttgagatc cagttcgatg    3180
taacccactc gtgcacccaa ctgatcttca gcatctttta ctttcaccag cgtttctggg    3240
tgagcaaaaa caggaaggca aaatgccgca aaaaagggaa taagggcgac acggaaatgt    3300
tgaatactca tactcttcct ttttcaatat tattgaagca tttatcaggg ttattgtctc    3360
atgagcggat acatatttga atgtatttag aaaaataaac aaatagggt tccgcgcaca    3420 tttccccgaa aagtgccacc tgacgtctaa gaaaccatta ttatcatgac attaacctat    3480 aaaaatag gc gtatcacgag gccctttcgt cttcaa                             3516
```

<210> SEQ ID NO 10
<211> LENGTH: 185
<212> TYPE: PRT
<213> ORGANISM: amino acid sequence of Staphylococcus aureus nucleus protein

<400> SEQUENCE: 10

Val Lys Gln Thr Thr Ile Ala Leu Ala Leu Leu Pro Leu Leu Phe Thr
 1               5                  10                  15

Pro Val Thr Lys Ala Arg Ile Gln Pro Ala Thr Ser Thr Lys Lys Leu
                20                  25                  30

His Lys Glu Pro Ala Thr Leu Ile Lys Ala Ile Asp Gly Thr Thr Val
            35                  40                  45

Lys Leu Met Tyr Lys Gly Gln Pro Met Thr Phe Arg Leu Leu Leu Val
        50                  55                  60

Asp Thr Pro Glu Phe Lys Ala Lys Ser Pro Lys Lys Ala Leu Glu Lys

-continued

```
                65                  70                  75                  80
Tyr Gly Pro Glu Ala Ser Ala Phe Thr Lys Lys Met Val Glu Asn Ala
                    85                  90                  95
Lys Lys Ile Glu Val Glu Phe Asp Lys Gly Gln Arg Thr Asp Lys Tyr
            100                 105                 110
Gly Arg Gly Leu Ala Tyr Ile Tyr Ala Asp Gly Lys Met Val Asn Glu
        115                 120                 125
Ala Leu Val Arg Gln Gly Leu Ala Lys Val Ala Tyr Val Tyr Lys Pro
    130                 135                 140
Asn Asn Thr His Glu Gln His Leu Arg Lys Ser Glu Ala Gln Ala Lys
145                 150                 155                 160
Lys Glu Lys Leu Asn Ile Trp Ser Glu Asp Asn Ala Asp Ser Gly Gln
                165                 170                 175
Val Asp Val His His His His His His
            180                 185

<210> SEQ ID NO 11
<211> LENGTH: 22
<212> TYPE: PRT
<213> ORGANISM: amino acid leader sequence of Staphylococcus aureus
      nuclease

<400> SEQUENCE: 11

Val Lys Gln Thr Thr Ile Ala Leu Ala Leu Leu Pro Leu Leu Phe Thr
 1               5                  10                  15

Pro Val Thr Lys Ala Arg
            20

<210> SEQ ID NO 12
<211> LENGTH: 78
<212> TYPE: DNA
<213> ORGANISM: oligonucleotide sequence from cAMP-dependent protein
      kinase

<400> SEQUENCE: 12
aattcggtgg tactacttac gctgatttta ttgcttctgg tagaactggt agaagaaatg      60
ctattcatga tggtggtc                                                   78

<210> SEQ ID NO 13
<211> LENGTH: 78
<212> TYPE: DNA
<213> ORGANISM: oligonucleotide sequence from cAMP-dependent protein
      kinase

<400> SEQUENCE: 13
tcgagaccac catcatgaat agcatttctt ctaccagttc taccagaagc aataaaatca      60
gcgtaagtag taccaccg                                                   78

<210> SEQ ID NO 14
<211> LENGTH: 78
<212> TYPE: DNA
<213> ORGANISM: oligonucleotide sequence from cAMP-dependent protein
      kinase

<400> SEQUENCE: 14
aattcggtgg tactacttac gctgatttta ttgcttctgg tagaactggt ggtggtaatg      60
ctattcatga tggtggtc                                                   78

<210> SEQ ID NO 15
```

```
<211> LENGTH: 78
<212> TYPE: DNA
<213> ORGANISM: oligonucleotide sequence from cAMP-dependent protein
      kinase

<400> SEQUENCE: 15
tcgagaccac catcatgaat agcattacca ccaccagttc taccagaagc aataaaatca      60
gcgtaagtag taccaccg                                                   78

<210> SEQ ID NO 16
<211> LENGTH: 20
<212> TYPE: PRT
<213> ORGANISM: cAMP-dependent protein kinase inhibitory peptide (PKI)
      sequence

<400> SEQUENCE: 16

Thr Thr Tyr Ala Asp Phe Ile Ala Ser Gly Arg Thr Gly Arg Arg Asn
 1               5                  10                  15

Ala Ile His Asp
             20

<210> SEQ ID NO 17
<211> LENGTH: 20
<212> TYPE: PRT
<213> ORGANISM: cAMP-dependent protein kinase non-inhibitory control
      peptide

<400> SEQUENCE: 17

Thr Thr Tyr Ala Asp Phe Ile Ala Ser Gly Arg Thr Gly Gly Gly Asn
 1               5                  10                  15

Ala Ile His Asp
             20

<210> SEQ ID NO 18
<211> LENGTH: 13
<212> TYPE: PRT
<213> ORGANISM: Autophosphorylation sequence from BCY1

<400> SEQUENCE: 18

Glu Phe Gly Gln Arg Arg Thr Ser Val Ser Gly Ala Leu
 1               5                  10
```